(12) United States Patent
Oliver

(10) Patent No.: US 10,294,516 B2
(45) Date of Patent: May 21, 2019

(54) ENHANCED PROBE BINDING

(71) Applicant: Nabsys 2.0 LLC, Providence, RI (US)

(72) Inventor: John S. Oliver, Bristol, RI (US)

(73) Assignee: NABSYS 2.0 LLC, Providence, RI (US)

( * ) Notice: Subject to any disclaimer, the term of this patent is extended or adjusted under 35 U.S.C. 154(b) by 0 days.

(21) Appl. No.: 14/157,136

(22) Filed: Jan. 16, 2014

(65) Prior Publication Data

US 2014/0212874 A1 Jul. 31, 2014

Related U.S. Application Data

(60) Provisional application No. 61/754,258, filed on Jan. 18, 2013.

(51) Int. Cl.
| | | |
|---|---|---|
| C12P 19/34 | (2006.01) | |
| C12Q 1/6825 | (2018.01) | |
| C12Q 1/6869 | (2018.01) | |
| C12Q 1/6827 | (2018.01) | |
| C12Q 1/6858 | (2018.01) | |

(52) U.S. Cl.
CPC ......... C12Q 1/6825 (2013.01); C12Q 1/6827 (2013.01); C12Q 1/6858 (2013.01); C12Q 1/6869 (2013.01)

(58) Field of Classification Search
USPC .......... 435/6.1, 6.11, 6.12, 91.1, 91.2, 91.51, 435/183, 283.1, 287.1, 287.2; 436/94, 436/501; 536/23.1, 24.3, 24.33, 25.3
See application file for complete search history.

(56) References Cited

U.S. PATENT DOCUMENTS

| | | |
|---|---|---|
| 3,699,437 A | 10/1972 | Ur |
| H201 H | 1/1987 | Yager |
| 4,810,650 A | 3/1989 | Kell et al. |
| 4,874,499 A | 10/1989 | Smith et al. |
| 5,194,133 A | 3/1993 | Clark et al. |
| 5,202,231 A | 4/1993 | Drmanac et al. |
| 5,246,552 A | 9/1993 | Kamiya et al. |
| 5,314,829 A | 5/1994 | Coles |
| 5,405,519 A | 4/1995 | Schwartz |
| 5,427,663 A | 6/1995 | Austin et al. |
| 5,455,166 A | 10/1995 | Walker |
| 5,539,082 A | 7/1996 | Nielsen et al. |
| 5,560,811 A | 10/1996 | Briggs et al. |

(Continued)

FOREIGN PATENT DOCUMENTS

| | | |
|---|---|---|
| DE | 19936302 A1 | 2/2001 |
| EP | 455508 A1 | 11/1991 |

(Continued)

OTHER PUBLICATIONS

Fish, (Wikipedia.com, accessed Nov. 2, 2014).

(Continued)

*Primary Examiner* — Frank W Lu
(74) *Attorney, Agent, or Firm* — Goodwin Procter LLP

(57) ABSTRACT

Methods for enhancing the binding of oligonucleotide probes to DNA and RNA are disclosed. The methods make use of thermodynamic and kinetic effects to reduce probe mismatches and failure of complementary probes to bind to DNA and RNA templates. Mapping and sequencing of the probed DNA and RNA samples are contemplated herein.

7 Claims, 22 Drawing Sheets

Specification includes a Sequence Listing.

(56) References Cited

U.S. PATENT DOCUMENTS

| | | |
|---|---|---|
| 5,599,664 A | 2/1997 | Schwartz |
| 5,650,305 A | 7/1997 | Hui et al. |
| 5,681,947 A | 10/1997 | Bergstrom et al. |
| 5,683,881 A | 11/1997 | Skiena |
| 5,720,928 A | 2/1998 | Schwartz |
| 5,744,366 A | 4/1998 | Kricka et al. |
| 5,773,571 A | 6/1998 | Nielsen et al. |
| 5,795,782 A | 8/1998 | Church et al. |
| 5,824,477 A | 10/1998 | Stanley |
| 5,837,115 A | 11/1998 | Austin et al. |
| 5,908,745 A | 6/1999 | Mirzabekov et al. |
| 5,928,869 A | 7/1999 | Nadeau et al. |
| 5,942,391 A | 8/1999 | Zhang et al. |
| 5,972,619 A | 10/1999 | Drmanac et al. |
| 6,015,714 A | 1/2000 | Baldarelli et al. |
| 6,020,599 A | 2/2000 | Yeo |
| 6,025,891 A | 2/2000 | Kim |
| 6,084,648 A | 7/2000 | Yeo |
| 6,096,503 A | 8/2000 | Sutcliffe et al. |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,270,965 B1 * | 8/2001 | Kleiber ............... C12Q 1/686 435/5 |
| 6,274,320 B1 | 8/2001 | Rothberg et al. |
| 6,294,136 B1 | 9/2001 | Schwartz |
| 6,294,325 B1 | 9/2001 | Wetmur |
| 6,303,288 B1 | 10/2001 | Furcht et al. |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,410,243 B1 | 6/2002 | Wyrick et al. |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 | 10/2002 | Golovchenko et al. |
| 6,497,138 B1 | 12/2002 | Abdel-Rahman et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,616,895 B2 | 9/2003 | Dugas et al. |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,706,203 B2 | 3/2004 | Barth et al. |
| 6,713,263 B2 | 3/2004 | Schwartz |
| 6,723,513 B2 | 4/2004 | Lexow |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,887,714 B2 | 5/2005 | Fritsch et al. |
| 6,905,586 B2 | 6/2005 | Lee et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 6,952,651 B2 | 10/2005 | Su |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,118,657 B2 | 10/2006 | Golovchenko et al. |
| 7,170,050 B2 | 1/2007 | Turner et al. |
| 7,176,007 B2 | 2/2007 | Cox et al. |
| 7,189,503 B2 | 3/2007 | Akeson et al. |
| 7,211,414 B2 | 5/2007 | Hardin et al. |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,257,987 B2 | 8/2007 | O'Brien et al. |
| 7,259,342 B2 | 8/2007 | Lin et al. |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,432,365 B1 | 10/2008 | O'Donnell et al. |
| 7,462,449 B2 | 12/2008 | Quake |
| 7,468,271 B2 | 12/2008 | Golovchenko et al. |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,625,706 B2 | 12/2009 | Akeson et al. |
| 7,670,770 B2 | 3/2010 | Chou et al. |
| 7,678,562 B2 | 3/2010 | Ling |
| 7,731,826 B2 | 6/2010 | Hibbs et al. |
| 7,744,816 B2 | 6/2010 | Su et al. |
| 7,824,859 B2 | 11/2010 | Sorge |
| 7,854,435 B2 | 12/2010 | Campbell |
| 7,867,782 B2 | 1/2011 | Barth |
| 7,897,344 B2 | 3/2011 | Dahl et al. |
| 7,939,259 B2 | 5/2011 | Kokoris et al. |
| 8,003,319 B2 | 8/2011 | Polonsky et al. |
| 8,133,719 B2 | 3/2012 | Drmanac et al. |
| 8,206,568 B2 | 6/2012 | Branton et al. |
| 8,232,055 B2 | 7/2012 | Bruhn et al. |
| 8,232,582 B2 | 7/2012 | Sauer et al. |
| 8,246,799 B2 | 8/2012 | Oliver et al. |
| 8,262,879 B2 | 9/2012 | Oliver |
| 8,278,047 B2 | 10/2012 | Oliver et al. |
| 8,278,050 B2 | 10/2012 | Bailey et al. |
| 8,333,934 B2 | 12/2012 | Cao et al. |
| 8,377,039 B2 | 2/2013 | Utterberg et al. |
| 8,455,260 B2 | 6/2013 | Goldstein et al. |
| 8,507,197 B2 | 8/2013 | Palaniappan |
| 8,574,892 B2 | 11/2013 | Su |
| 8,592,182 B2 | 11/2013 | Kokoris et al. |
| 8,628,919 B2 | 1/2014 | Xiao et al. |
| 8,715,933 B2 | 5/2014 | Oliver |
| 8,882,980 B2 | 11/2014 | Ling et al. |
| 8,926,813 B2 | 1/2015 | Oliver |
| 9,650,668 B2 | 5/2017 | Oliver et al. |
| 9,702,003 B2 | 7/2017 | Goldstein |
| 9,719,980 B2 | 8/2017 | Oliver |
| 2002/0028458 A1 | 3/2002 | Lexow |
| 2002/0061588 A1 * | 5/2002 | Jacobson ............... C12N 13/00 435/446 |
| 2002/0108136 A1 | 8/2002 | Pati et al. |
| 2002/0127855 A1 | 9/2002 | Sauer et al. |
| 2002/0131902 A1 | 9/2002 | Levy |
| 2002/0150961 A1 | 10/2002 | Bogyo et al. |
| 2003/0003609 A1 | 1/2003 | Sauer et al. |
| 2003/0064095 A1 | 4/2003 | Martin et al. |
| 2003/0104428 A1 | 6/2003 | Branton et al. |

(56) References Cited

U.S. PATENT DOCUMENTS

| | | |
|---|---|---|
| 2003/0143614 A1 | 7/2003 | Drmanac |
| 2003/0186256 A1 | 10/2003 | Fischer |
| 2003/0208165 A1 | 11/2003 | Christensen et al. |
| 2004/0137734 A1 | 7/2004 | Chou et al. |
| 2004/0146430 A1 | 7/2004 | Dugas |
| 2005/0019784 A1 | 1/2005 | Su et al. |
| 2005/0202444 A1 | 9/2005 | Zhu |
| 2006/0057025 A1 | 3/2006 | Eversmann et al. |
| 2006/0194306 A1 | 8/2006 | Herr et al. |
| 2006/0269483 A1 | 11/2006 | Austin et al. |
| 2006/0287833 A1 | 12/2006 | Yakhini |
| 2007/0039920 A1 | 2/2007 | Kutchoukov et al. |
| 2007/0042366 A1 | 2/2007 | Ling |
| 2007/0054276 A1 | 3/2007 | Sampson |
| 2007/0084163 A1 | 4/2007 | Lai |
| 2007/0178240 A1 | 8/2007 | Yamazaki et al. |
| 2007/0190524 A1 | 8/2007 | Mauclere et al. |
| 2007/0190542 A1 | 8/2007 | Ling et al. |
| 2007/0218471 A1 | 9/2007 | Kim et al. |
| 2007/0238112 A1 | 10/2007 | Sohn et al. |
| 2008/0085840 A1 | 4/2008 | Buzby |
| 2008/0119366 A1 | 5/2008 | Sauer et al. |
| 2008/0242556 A1 | 10/2008 | Cao et al. |
| 2008/0254995 A1 | 10/2008 | Kim et al. |
| 2008/0305482 A1 | 12/2008 | Brentano et al. |
| 2009/0005252 A1 | 1/2009 | Drmanac et al. |
| 2009/0011943 A1 | 1/2009 | Drmanac et al. |
| 2009/0099786 A1 | 4/2009 | Oliver et al. |
| 2009/0111115 A1 | 4/2009 | Drmanac et al. |
| 2009/0136948 A1 | 5/2009 | Han et al. |
| 2009/0214392 A1 | 8/2009 | Kameoka et al. |
| 2009/0216216 A1 | 8/2009 | Powers et al. |
| 2009/0299645 A1 | 12/2009 | Colby et al. |
| 2010/0096268 A1 | 4/2010 | Ling et al. |
| 2010/0143960 A1 | 6/2010 | Bazin |
| 2010/0203076 A1 | 8/2010 | Fotin-Mleczek et al. |
| 2010/0214162 A1 | 8/2010 | Talbot et al. |
| 2010/0243449 A1 | 9/2010 | Oliver |
| 2010/0297644 A1 | 11/2010 | Kokoris et al. |
| 2010/0310421 A1 | 12/2010 | Oliver et al. |
| 2012/0052079 A1 | 3/2012 | Richardson et al. |
| 2012/0074925 A1 | 3/2012 | Oliver |
| 2012/0208193 A1 | 8/2012 | Okino et al. |
| 2012/0214162 A1* | 8/2012 | Oliver .................. C12Q 1/6816 435/6.11 |
| 2012/0222958 A1 | 9/2012 | Pourmand et al. |
| 2013/0011934 A1 | 1/2013 | Oliver et al. |
| 2013/0085473 A1 | 4/2013 | Weilbacher et al. |
| 2014/0087390 A1 | 3/2014 | Oliver et al. |
| 2014/0174927 A1 | 6/2014 | Bashir et al. |
| 2014/0224356 A1 | 8/2014 | Hatton et al. |

FOREIGN PATENT DOCUMENTS

| | | | |
|---|---|---|---|
| EP | 0958495 A1 | 11/1999 | |
| EP | 1486775 A1 | 12/2004 | |
| EP | 1685407 A1 | 8/2006 | |
| JP | 2002526759 A | 8/2002 | |
| JP | 2003-028826 A | 1/2003 | |
| JP | 2003510034 A | 3/2003 | |
| JP | 2003513279 A | 4/2003 | |
| JP | 2004004064 A | 1/2004 | |
| JP | 2007068413 A | 3/2007 | |
| WO | WO-1990004652 A1 | 5/1990 | |
| WO | WO-1993022678 A2 | 11/1993 | |
| WO | WO-1996017957 A1 | 6/1996 | |
| WO | WO-2008069973 | 11/1997 | |
| WO | WO-1998035012 A2 | 8/1998 | |
| WO | WO-2000009757 A1 | 2/2000 | |
| WO | WO-2000011220 A1 | 3/2000 | |
| WO | WO-2000020626 A1 | 4/2000 | |
| WO | WO-2000022171 A2 | 4/2000 | |
| WO | WO-0056937 | 9/2000 | |
| WO | WO-2000062931 A1 | 10/2000 | |
| WO | WO-0079257 A1 | 12/2000 | |
| WO | WO-2001018246 A1 | 3/2001 | |
| WO | WO-2001031063 A1 | 5/2001 | |
| WO | WO-2001033216 A1 | 5/2001 | |
| WO | WO-2001037958 A2 | 5/2001 | |
| WO | WO-2001042782 A1 | 6/2001 | |
| WO | WO-2001046467 A2 | 6/2001 | |
| WO | WO-2002007199 A1 | 1/2002 | |
| WO | WO-2002050534 | 6/2002 | |
| WO | WO-02066595 A1 | 8/2002 | |
| WO | WO-2003000920 A2 | 1/2003 | |
| WO | WO-2003010289 A2 | 2/2003 | |
| WO | WO-2003079416 A1 | 9/2003 | |
| WO | WO-2003089666 A2 | 10/2003 | |
| WO | WO-2003106693 A2 | 12/2003 | |
| WO | WO-2004035211 A1 | 4/2004 | |
| WO | WO-2004085609 A2 | 10/2004 | |
| WO | WO-2005017025 A2 | 2/2005 | |
| WO | WO-200645 A1 | 1/2006 | |
| WO | WO-2006020775 A2 | 2/2006 | |
| WO | WO-2006028508 A2 | 3/2006 | |
| WO | WO-2006052882 | 5/2006 | |
| WO | WO-2007021502 A1 | 2/2007 | |
| WO | WO-2007041621 | 4/2007 | |
| WO | WO-2007084076 A1 | 7/2007 | |
| WO | WO-2007106509 | 9/2007 | |
| WO | WO-2007109228 A1 | 9/2007 | |
| WO | WO-2007111924 | 10/2007 | |
| WO | WO-2007127327 | 11/2007 | |
| WO | WO-2008021488 | 2/2008 | |
| WO | WO-2008039579 | 4/2008 | |
| WO | WO-2008042018 | 4/2008 | |
| WO | WO-2008046923 | 4/2008 | |
| WO | WO-2008049021 | 4/2008 | |
| WO | WO-2008079169 | 7/2008 | |
| WO | WO-2009046094 A1 | 4/2009 | |
| WO | WO-2010002883 A2 | 1/2010 | |
| WO | WO-2010111605 A2 | 9/2010 | |
| WO | WO-2010138136 A1 | 12/2010 | |
| WO | WO-2011109825 A2 | 9/2011 | |
| WO | WO-2012109574 A2 | 8/2012 | |
| WO | WO-2013016486 A1 | 1/2013 | |
| WO | WO-2014052433 A2 | 4/2014 | |

OTHER PUBLICATIONS

Fungi, (Wikipedia.com; accessed Jun. 3, 2013).
How many species of bacteria are there (wisegeek.com; accessed Jan. 21, 2014).
Howorka et al., "Sequence-specific detection of individual DNA strands using engineered nanopores", nature biotechnology, vol. 19, Jul. 2001.
International Preliminary Report on Patentability dated Apr. 9, 2015 in PCT/US2013/061651, 10 pages.
List of sequenced bacterial genomes (Wikipedia.com; accessed Jan. 24, 2014).
Mammal, (Wikipedia.com; accessed Sep. 22, 2011).
Murinae, (Wikipedia.com, accessed Mar. 18, 2013).
Plant, (Wikipedia.com; accessed Mar. 8, 2013).
Vercoutere et al., "Rapid discrimination among individual DNA hairpin molecules at single-nucleotide resolution using an ion channel" nature biotechnology, vol. 19, Mar. 2001.
Viruses (Wikipedia.com, accessed Nov. 24, 2012).
Decision to Grant dated Aug. 21, 2014 in European Patent Application No. 10 717 908.7-1559.
Examination Report dated Jun. 11, 2014 in European Patent Application No. 11 785 507.2-1404, 8 pages.
Examination Report dated Jun. 3, 2014 in European Patent Application No. 08 835 216.6, 5 pages.
Examination Report dated Oct. 23, 2014 in European Patent Application No. 11 785 257.4-1404, 6 pages.
Examination Report dated Oct. 29, 2014 in European Patent Application No. 09 748 871.2-1408, 5 pages.
Intention to Grant dated Jun. 26, 2014 in European Patent Application No. 10 717 908.7-1559.

(56) References Cited

OTHER PUBLICATIONS

Intention to Grant dated Mar. 25, 2014 in European Patent Application No. 10 717 908.7-1559.
International Search Report and Written Opinion dated Jul. 29, 2014, PCT/US13/061651, 16 pages.
International Search Report and Written Opinion dated Jul. 29, 2014, PCT/US14/021756, 11 pages.
International Search Report and Written Opinion dated Jun. 26, 2014, PCT/US14/011829, 16 pages.
Notice of Final Rejection dated Jul. 2, 2014 in Japanese Patent Application No. 2011-525300.
Stephen et al., "DNA manipulation sorting, and mapping in nanofluidic systems," Chemical Society Reviews, vol. 39, No. 3, Jan. 1, 2010, p. 1133.
Thompson et al., "Detection of Structural Variations Using Nanodetector Positional Sequencing," AGBT Meeting, Feb. 1, 2012.
Thompson et al., "Mapping and sequencing DNA using nanopores and nanodetectors," Electrophoresis, vol. 33, No. 23, Dec. 12, 2012, pp. 3429-3436.
Thompson et al., "Structural Variations Identified Using Solid-State Nanodetectors," Meeting of the American Society for Human Genetics, Nov. 9, 2012.
Wu et al., "On-column conductivity detection in capillary-chip electrophoresis", 2007, 28, 4612-4619.
Broude et al. (1994) Enhanced DNA sequencing by hybridization, Proc. Natl. Acad. Sci. USA, 91, 3072-3076.
Akeson, et al., "Microsecond time-scale discrimination among polycytidylic acid, polyadenylic; acid, and polyuridylic acid as homopolymers or as segments within single RNA molecules,"; Biophys. J. 77, 3227-3233 (1999).
Alberts, B., et al., (1970) "T4 Bacteriophage Gene 32: A Structural Protein in the Replication and Recombination of DNA," Nature 227:1313-1318.
Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.
Anderson, P. et al., "Nkx3.1 and Myc crossregulate shared target genes in mouse and human prostate tumorigenesis," J. Clinical Investigation, May 2012, pp. 1907-1919, vol. 122, http://www.jci.org.
Arratia, R., et al., (1989) "Poisson Process Approximation for Repeats in One Sequence and Its Application to Sequencing by Hybridization," Dept. of Mathematics, University of Southern California.
Arrowsmith, C. et al., "Epigenetic protein families: a new frontier for drug discovery," Nature Reviews: Drug Discovery, May 2012, pp. 384-400, vol. 11, Macmillan Publishers Limited.
Ashkin, "Optical trapping and manipulation of neutral particles using lasers," Proc. Natl.; Acad. Sci. USA, vol. 94, DD. 4853-4860, May 1997.
Austin, M., et al., (2004) "Fabrication of 5 nm Linewidth and 14 nm Pitch Features by Nanoimprint Lithography," App. Phys. Lett. 84:5299-5301.
Austin, Robert, "The art of sucking spaghetti", Nature Publishing Group, Nature Materials, vol. 2, pp. 567-568, Sep. 2003.
Bains, W. et al., (1988) "A Novel Method for Nucleic Acid Sequence Determination," J. Theor. Biol. 135:303-307.
Baliga, R., et al., (2001) "Kinetic Consequences of Covalent Linkage of DNA Binding Polyamides," Biochemistry 40:3-8.
Ben-Dor et al, "On the Complexity of Positional Sequencing by Hybridization", Journal of Computational Biology, vol. 8, No. 4, 2001, pp. 361-371.
Bennett et al., (2005) "Toward the $1000 Human Genome," Pharmacogenomics 6:373-382.
Bianco, P., et al., "Interaction of the RecA Protein of *Escherichia coli* with Single-Stranded Oligodeoxyribonucleotides," Nucleic Acids Research vol. 24. No. 24 (1996) 4933-4939.
Bloom, et al, Applications of Numbered Undirected Graphs, Proceedings of the IEEE, vol. 65, No. 4, Apr. 1977, pp. 562-570.

Bourdoncle, A., et al., "Quaruplex-Based Molecular Beacons as Tunable DNA Probes", J. Am. Chem. Soc., vol. 128, No. 34, pp. 11094-11105, 2006.
Branton, Daniel et al, "The potential and challenges of anopore sequencing," Nature Biotechnology, vol. 26, No. 10, Oct. 2008, pp. 1146-1153.
Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.
Buchmueller, K.L., et. al., (2006) "Physical and Structural Basis for the Strong Interactions of the -ImPy—Central Pairing Motif in the Polyamide f-ImPylm," Biochemistry 45:13551-13565.
Cao, H., et al., (2002) "Fabrication of 10 nm Enclosed Nanofluidic Channels," Applied Physics Letters 81(1): 174-176.
Cao, H., et al., (2002) "Gradient Nanostructures for Interfacing Microfluidics and Nanofluidics," Applied Physics Letters 81:3058-3060.
Chen, C., et al., (1994) "Analogous Organic Synthesis of Small-Compound Libraries: Validation of Combinatorial Chemistry in Small-Molecule Synthesis," J. Am. Chem. Soc. 116:2661-2662.
Chen, P., et al., (2004) "Probing Single DNA Molecule Transport Using Fabricated Nanopores," Nano Letters 4:2293-2298.
Chetverin, A., et al., (1994) "Oligonucleotide Arrays: New Concepts and Possibilities," Bio/Technology 12:1093-1099.
Cox, M. (2007) "Motoring Along with the Bacterial RecA Protein," Nature Reviews—Molecular Cell Biology 9:127-138.
Dervan, P.B. (2001) "Molecular Recognition of DNA by Small Molecules," Bioorg. Med. Chem. 9:2215-2235.
Dervan, P.B., et al., (2003) "Recognition of the DNA minor groove by pyrrole-imidazole polyamides," Curr. Op. Struc. Biol. 13:284-299.
Doss, R.M., et al., (2006) "Programmable Oligomers for Minor Groove DNA Recognition," J. Am. Chem. Soc. 128:9074-9079.
Drmanac, R., et al. (1989) "Sequencing of Megabase Plus DNA by Hybridization: Theory of the Method," Genomics 4:114-128.
Drmanac, R., et al. (2002) "Sequencing by Hybridization (SBH): Advantages, Achievements, and Opportunities," Advances in Biochemical Engineering/Biotechnology, vol. 77: 75-101.
Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.
Examination Report dated Feb. 7, 2013 in European Application No. 10 717 908.7-1240 (4 pages).
Examination Report dated Mar. 4, 2013 in European Application No. 08 835 216.6-1404 (6 pages).
Farkas, Z., et al., (2003) "DNA Uptake Into Nuclei: Numerical and Analytical Results," J. Phys.: Condens. Matter 15:S1767-S1777.
Fechter, E.J., et al., (2005) "Sequence-specific Fluorescence Detection of DNA by Polyamide-Thiazole Orange Conjugates," J. Am. Chem. Soc. 127:16685-16691.
Floreancig, P.E., et al., (2000) "Recognition of the Minor Groove of DNA by Hairpin Polyamides Containing α-Substituted-,β-Amino Acids," J. Am. Chem. Soc. 122:6342-6350.
Fodor, S., et al., (2005) "Light-Directed, Spatially Addressable Parall Chemical Synthesis" Research Article 6 pgs.
Fologea, D., et al., (2005) "Slowing DNA Translocation in a Solid-State Nanopore" Nano Lett 5(9):1734-7.
Frieze, A., et al., (1999) "Optimal Reconstruction of a Sequence From its Probes," 12 pgs.
Gerland, U., et al., (2004) "Translocation of Structured Polynucleotides Through Nanopores," Phys. Biol. 1:19-26.
Gershow, M., et al., (2007) "Recapturing and Trapping Single Molecules with a Solid-State Nanopore," Nature Nanotech. 2:775-779.
Ghosh, et al, Detection of Double-Stranded DNA: molecular methods and applications for DNA diagnostics Molecular Biosystems (2006) vol. 2, pp. 551-560.
Giehart B., et al., (2008) "Nanopore with transverse nanoelectrodes for electrical characterization and sequencing of DNA" Sensors and Actuators B., Elsevier Sequoia S.A, ScienceDirect,132:2 pp. 593-600.

(56) References Cited

OTHER PUBLICATIONS

Gracheva, M., et al., (2002) "Simulation of the Electric Response of DNA Translocation through a Semiconductor Nanopore-Capacitor," Nanotechnology 17:622-633.
Greer, E. et al., "Histone methylation: a dynamic mark in health, disease and inheritance," Nature Review: Genetics, May 2012, pp. 343-357, vol. 13, Macmillan Publishers Limited.
Guo, L. (2004) "Recent Progress in Nanoimprint Technology and its Application," J. Phys. D: Appl. Phys 37:R123-R141 (Appendices B-D).
Gygi, M.P., et al., (2002) "Use of fluorescent sequence-specific polyamides to discriminate human chromosomes by microscopy and flow cytometry," Nucleic Acids Research 30:2790-2799.
Halby, L., et al., (2005) "Functionalized head-to-head hairpin polyamides: Synthesis, double-stranded DNA-binding activity and affinity," Bioorg. Med. Chem. Lett. 15:3720-3724.
Hannenhalli S. et al. Comput Appl Biosci (1996) 12 (1): 19-24.
Heller, C., (2001) "Principles of DNA Separation with Capillary Electrophoresis," Electrophoresis 22:629-643.
Heng, J., et al., (2004) "Sizing DNA Using a Nanometer-Diameter Pore," Biophysical Journal 87:2905-2911.
Heyn, H. et al., "DNA methylation profiling in the clinic: applications and challenges," Nature Review: Genetics, Oct. 2012, pp. 679-692, vol. 13, Macmillan Publishers Limited.
Hudson, B., (1999) "An Experimental Study of SBH with Gapped Probes," 50 pgs.
International Preliminary Report on Patentability in PCT/US2012/024708 dated Aug. 13, 2013.
International Preliminary Report on Patentability dated Apr. 7, 2010, PCT/US2008/078432.
International Preliminary Report on Patentability, Application No. PCT/US2009/055878, dated Nov. 29, 2011, 9 pages.
International Preliminary Report on Patentability, Application No. PCT/US2010/028848, dated Sep. 27, 2011, 8 pages.
International Preliminary Report on Patentability, Application No. PCT/US2011/053274, dated May 28, 2013, 14 pages.
International Preliminary Report on Patentability, Application No. PCT/US2011/059933, dated May 21, 2013, 8 pages.
International Preliminary Report on Patentability, dated Mar. 8, 2011, Application No. PCT/US2009/055876.
International Search Report and Written Opinion dated Feb. 10, 2010, PCT/US09/558876, 5 pages.
International Search Report and Written Opinion dated Feb. 5, 2009, PCT/US08/078432.
International Search Report and Written Opinion dated Jun. 29, 2010, PCT/US09/055876, 10 pages.
International Search Report and Written Opinion dated Mar. 24, 2010, PCT/US09/055878, 13 pages.
International Search Report and Written Opinion dated Oct. 25, 2012, PCT/US12/024708.
International Search Report and Written Opinion dated Sep. 30, 2010, PCT/US2010/028848, 14 pages.
International Search Report and Written Opinion, PCT/US2011/053274, dated May 2, 2013.
International Search Report and Written Opinion, PCT/US2011/059933, dated Apr. 2, 2012.
International Search Report for PCT/US04/04138, dated May 4, 2006, 5 pages.
Invitation to Pay Additional Fees and, Where Applicable, Protest Fee & Partial International Search dated Aug. 19, 2010, PCT/US2010/028848, 7 pages.
Invitation to Pay Additional Fees and, Where Applicable, Protest Fee & Partial International Search dated Feb. 15, 2013, PCT/US2011/053274, 9 pages.
Invitation to Pay Additional Fees and, Where Applicable, Protest Fee & Partial International Search dated Jul. 10, 2012, PCT/US2012/024708, 10 pages.
Invitation to Pay Additional Fees and, Where Applicable, Protest Fee & Partial International Search dated Mar. 3, 2014, PCT/US2012/061651, 5 pages.
Jonsson, U., et al., (1991) "Real-Time Biospecific Interaction Analysis Using Surface Plasmon Resonance and a Sensor Chip Technology," BioTechniques, 11:620-627.
Ju et al., "Four-color DNA Sequencing by Synthesis Using Cleavable Fluorescent Nucleotide Reversible Terminators," Proc. Nat. Acad. Sci. USA (2006) 103:19635-19640.
Kalaugher, L., (2002) "Diffraction Gradient Lithography Aids Nanofluidics," Nanotechweb.org.
Kanehisa, L. (1984) "Use of Statistical Criteria for Screening Potential Homologies in Nucleic Acid Sequences," Nucleic Acids Research 12:203-213.
Kasianowicz et al., "Characterization of Individual Polynucleotide Molecules Using a Membrane Channel," Proc. Nat. Acad. Sci. USA 93:13770-13773 (1996).
Khrapko, K.R., et al., (1989) "An Oligonucleotide Hybridization Approach to DNA Sequencing," FEBS Lett. 256:118-22.
Kim, C., et al., (1992) "Binding Properties of Replication Protein A from Human and Yeast Cells," Mol. and Cell. Bio. 12(7):3050-3059.
Koike, Shinji et al., "Investigation into the Degrading Mechanism of Positive Electrodes after Calendar Life Test Using Transmission Electron Microscopy", 214th ECS Meeting, Abstract #569, The Electrochemical Society, Osaka, Japan, 1 page.
Kuo, et al., "Hybrid three-dimensional nanofluidic/microfluidic devices using; molecular gates," Sensors and Actuators A, vol. 102 (Oct. 2002):223-233.
Langa, "Self-organized growth of single crystals of nanopores," Applied Physics Letters, AIP, American Institute of Physics, 2003, vol. 82, No. 2, pp. 278-280.
Langer-Safer, P. et al., "Immunological method for mapping genes on *Drosophila polytene* chromosomes," Proc. Natl. Acad. Sci. USA, Jul. 1982, pp. 4381-4385, vol. 79.
Lennon, Erwan et al., "Evaporative Pumping of Liquid in Nanochannel for Electrical Measurement of a Single Biomolecule in Nanofluidic Format", Proceedings of the 7th IEEE Internation Conference on Nantechnology, Hong Kong, Aug. 2-5, 2007.
Li et al., "Ion-beam sculpting at nanometre length scales", Nature 412,166-169 (2001).
Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.
Liang, X., et al., (2008) "Nanogap Detector Inside Nanofluidic Channel for Fast Real Time Label-Free DNA Analysis," Nano Letters 8:1472-76.
Loakes, D., et al., (1994) "5-Nitroindole as an Universal Base Analogue," Nucleic Acids Research 22:4039-4043.
Loakes, D., et al., (1995) "3-Nitropyrrole and 5-Nitroindole as Universal Bases in Primers for DNA Sequencing and PCR," 23:2361-2366.
Lohman, T., et al., (1994) "*Escherichia coli* Single-Stranded DNA-Binding Protein: Multiple DNA-Binding Modes and Cooperatives," Annu. Rev. Biochem. 63:527-70.
Losi, et al., "Time-Resolved Absorption and Photothermal Measurements with Recombinant; Sensory Rhodopsin II from Natronobacterium pharaonis," Biophys. J. 77, 3277-3286,; Dec. 1999.
Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].
Margulies et al., (2005) "Genome Sequencing in Microfabricated High-Density Picolitre Reactors," Nature 437:376-380.
Marques, M.A., et al., (2004) "Expanding the Repertoire of Heterocycle Ring Pairs for Programmable Minor Groove DNA Recognition," J. Am. Chem. Soc. 126:10339-10349.
McEntee, K., et al. "Binding of the RecA Protein of *Escherichia coli* to Single- and Double-Stranded DNA." J. Biol. Chem. (1981) 256:8835.
Meller, A., et al., (2000) "Rapid Nanopore Discrimination Between Single Polynucleotide Molecules," PNAS 97:1079-1084.
Meller, et al., "Voltage-driven DNA translocations through a nanopore," Phys. Rev. Lett.; 86(15),3435-3438 (2001).

(56) References Cited

OTHER PUBLICATIONS

Nice, E., et al., (1993) "Mapping of the Antibody- and Receptor-Binding Domains of Granulocyte Colony-Stimulating Factor Using an Optical Biosensor," Journal of Chromatography 646:159-168.
Nichols, R., et al., (1994) "A Universal Nucleoside for Use at Ambiguous Sites in DNA Primers," Letters to Nature, 369:492-493.
Notice of Reasons for Rejection dated Jun. 17, 2013 in Japanese Patent Application No. 2011-525300.
Notification of the First Office Action dated Sep. 28, 2012 in Chinese Patent Application No. 200980140663.0.
Notification of the Second Office Action dated Apr. 2, 2013 in Chinese Patent Application No. 200980140663.0.
Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.
Olasagasti, F.; Lieberman, K. R.; Benner, S.; Cheri, G. M.; Dahl, J. M.; Deamer, D. W.; Akeson, M. *Nat. Nanotechnol.* 2010, 5, 798-806.
Pablo, P.J., et al., (2000) "Absence of dc-Conductivity." Phys. Rev. Lett. 85:4992-4995.
Park, P., "ChIP-seq: advantages and challenges of a maturing technology," Nature Reviews: Genetics, Oct. 2009, pp. 669-680, vol. 10, Macmillan Publishers Limited.
Partial International Search Report dated Feb. 15, 2010, PCT/US09/055878, 3 pages.
Pastor, W. et al., "Genome-wide mapping of 5-hydroxymethylcytosine in embryonic stem cells," Nature, May 19, 2011, pp. 394-397, vol. 473, Macmillan Publishers Limited.
Perry, J., et al., (2005) "Review of Fabrication of Nanochannels for Single Phase Liquid Flow," 3rd Intl. Conference on Microchannels and Minichannels, Paper No. ICMM2005-75104.
Pevzner, P. et al., (1991) "Improved Chips for Sequencing by Hybridization," Journal of Biomolecular Structure & Dynamics 9:399-410.
Powell, M., et al., (1993) "Characterization of the Pf3 Single-Strand DNA Binding Protein by Circular Dichroism Spectroscopy," Biochemistry 32:12538-12547.
Preparata, F., et al., (1999) "On the Power of Universal Bases in Sequencing by Hybridization," 7 pgs.
Preparata, F.P., et. al., (2000) "Sequencing-by-Hybridization at the Information-Theory Bound: An Optimal Algorithm," J. Comp. Biol. 7: 621-630.
Quake et al., (2003) "Sequence information can be obtained from single DNA molecules," Proc. Nat. Acad. Sci. USA 100:3960-3964.
Rapley, Ralph, "Enhancing PCR Amplification and Sequencing Using DNA-Binding Proteins", Molecular Biotechnology, vol. 2, pp. 295-298, 1994.
Rehrauer, William M. et al., "Alteration of the Nucleoisude Triphosphate (NTP) Catalytic Domain within *Escherichia coli* recA Protein Attenuates NTP Hydrolysis but Not Joint Molecule Formation", pp. 1292-1297, The Journal of Biological Chemistry, The American Society for Biochemistry and Molecule Biology, Inc., vol. 268, No, 2, Jan. 15, 1993.
Riccelli, P. V. et al., "Hybridization of single-stranded DNA targets to immobilized complementary DNA probes: comparison of hairpin versus linear capture probes", Oxford University Press, Nucleic Acids Research, vol. 29, No. 4, pp. 996-1004, 2001.
Riehn, R. et al., "Restricting Mapping in Nanofluidic Devices," Proceedings of the National Academy of Sciences of the United States of America, (2005) 102:1012-10016.
Robertson, J., et al., (2007) "Single-Molecule Mass Spectrometry in Solution Using a Solitary Nanopore," PNAS 104:8207-8211.
Ross-Innes, C. et al., "Differential oestrogen receptor binding is associated with clinical outcome in breast cancer," Nature, Jan. 2012, pp. 389-394, vol. 481, Macmillan Publishers Limited.
Rucker, V.C., et al., (2003) "Sequence Specific Fluorescence Detection of Double Strand DNA," J. Am. Chem. Soc. 125:1195-1202.
Salpea, P. et al., "Postnatal development- and age-related changes in DNA-methylation patterns in the human genome," Nucleic Acids Research, 2012, pp. 6477-6494, vol. 40, No. 14, Oxford University Press.
Sanger, F. et al., (1977) "DNA Sequencing with Chain-Terminating Inhibitors," Proc. Natl. Acad. Sci. USA 12:5463-5467.
Shim et al., "Detection and Quantification of Methylation in DNA using Solid-State Nanopores", Scientific Reports, www.nature.com, Mar. 11, 2013, pp. 1-8.
Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.
Shoaib, M. et al., "PUB-NChIP-"In vivo biotinylation" approach to study chromatin in proximity to a protein of interest," Genome Research, 2013, pp. 331-340, vol. 23, Cold Spring Harbor Laboratory Press, www.genome.org.
Singer, E. (2008) "The $100 Genome," Technology Review 4 pgs.
Smeets, R., et al., (2008) "Translocation of RecA-Coated Double-Stranded DNA through Solid-State Nanopores," Nano Letters pp. A-G.
Southern, E.M. (1996) "DNA Chips: Analysing Sequence by Hybridization to Oligonucleotide on a Large Scale," Trends in Genetics 12(3):110-115.
Storm, A., et al., (2005) "Fast DNA Translocation through a Solid-State Nanopore," Nano Letters 5(7):1193-1197.
Storm, et al., "Fabrication of solid-state nanopores with single-nanometre precision," Nature; Materials 2,537-540, Aug. 2003.
Strezoska, Z., et al., (1991) "DNA Sequencing by Hybridization: 100 Bases Read by a Non-Gel-Based Method," Proc. Natl. Acad. Sci. USA 88:10089-10093.
Tegenfeldt, J., et al., (2004) "The Dynamics of Genomic-Length DNA Molecules in 100 nm Channels," Proc. Nat. Acad. Sci. USA 101:10979-10983.
Tersoff, "Less is more," Nature 412, 135-136, Jul. 2001.
Terwilliger, T., et al., (1996) "Gene V Protein Dimerization and Cooperativity of Binding to Poly (dA)," Biochemistry 35:16652-16664.
Tucker, P., et al., (1994) "Crystal Structure of the Adenovirus DNA Binding Protein a Hook-On Model for Cooperative DNA Binding," The EMBO Journal 13(13):2994-3002.
Urbach, A.R., (2001) "Toward rules for 1:1 polyamide:DNA recognition," PNAS 98:4343-4348.
Van Steensel, B. et al., "Identification of in vivo DNA targets of chromatin proteins using tethered Dam methyltransfarase," Nature Biotechnology, Apr. 2000, pp. 424-428, vol. 18.
Venkatesan et al., "Stacked Graphene-Al2O3 Nanopore Sensors for Sensitive Detection of DNA and DNA-Protein Complexes", www.acsnano.org, vol. 6, No. 1, 2012, pp. 441-450.
Warren, C.L., et al., (2006) "Defining the Sequence-Recognition Profile of DNA-Binding Molecules," PNAS 103:867-872.
Warren, S., (1996) "The Expanding World of Trinucleotide Repeats," Science 271:1374-1375.
Waugh, David S., "Make the most of affinity tags", pp. 316-320, Trends in Biotechnology, Science Direct, vol. 23, No. 6, Jun. 2005.
Web article (2003) "DNA Combed Into Nanochannels," http://www.nature.com.
Written Opinion dated Jul. 1, 2008, PCT/US06/38748, 6 pages.
Zhang, W., et al., (2006) "Discrimination of Hairpin Polyamides with an α-Substituted-γ-aminobutyric Acid as a 5'-TG-3' Reader in DNA Minor Groove," J. Am. Chem. Soc. 128:8766-8776.
Zwolak, M., et al., (2008) "Colloquium: Physical Approaches to DNA Sequencing and Detection." Rev. Mod. Phy. 80:141-165 (J).
Optical Tweezers: Introduction to Optical Tweezers, Retrieved Sep. 29, 2003 from http://www.nbi.dk/-tweezer/introduction.htm, pp. 1-5.
International Preliminary Report on Patentability dated Sep. 24, 2015 in PCT/US2014/021756, 8 pages.
Communication dated Oct. 20, 2015 in European Patent Application No. 11 785 507.2, 8 pages.
Intention to Grant dated Oct. 20, 2015 in European Patent Application No. 11 785 257.4-1404.
Official action in Japanese Patent Application No. 2013-538841 dated Nov. 12, 2015 9 pages.

(56) References Cited

OTHER PUBLICATIONS

Examination Report in European Patent Application No. EP 09 807 476.8-1554 dated Apr. 1, 2015 6 pages.
Examination Report in European Patent Application No. EP 09 748 871.2-1408 dated Sep. 9, 2015 4 pages.
Notification of Reexamination in Chinese Patent Application No. 200980140663.0 dated Nov. 25, 2015 19 pages.
Final Office Action in Japanese Patent Application No. 2014-218935 dated Jan. 4, 2016 one page.
Office Action in Japanese Patent Application No. 2014-218935 dated Jul. 27, 2015 2 pages.
Notice of Reasons for Rejection in Japanese Patent Application No. 2013-530398 dated Sep. 14, 2015.
Office Action in European Patent Application No. 08 835 216.6 dated Mar. 24, 2016 1 page.
Decision to Grant dated Mar. 10, 2016 in European Patent Application No. 11785257.4.
Examination Report dated Apr. 25, 2016 in European Patent Application No. 13 792 116.9-1408 6 pages.
Notice of Allowance in Japanese Patent Application No. 2013-538841 dated Jul. 7, 2016 3 pages.
"About Lock-In Amplifiers" (Stanford Research), last modified Jan. 19, 2004 and accessed Mar. 29, 2016 at http://www.thinksrs.com/downloads/PDFs/ApplicationNotes/Aboutl.IAS.pdf.
Kasianowicz, et al., "Characterization of individual polynucleotide molecules using a membrane channel," Proc. Natl. Acad. Sci., vol. 93, pp. 13770-13773, Nov. 1996.
Laugere, et al., "On-Chip Contactless Four-Electrode Conductivity Detection for Capillary Electrophoresis Devices," Analytical Chemistry, vol. 75, pp. 306-312, Jan. 2003.
Communication Pursued to Article 94(3) EPC dated Aug. 30, 2016 in European Patent Application No. 14 706 709.4, 3 pages.
Notice of Reasons for Rejection in Japanese Patent Application No. 2013-530398 dated Aug. 25, 2016.
International Preliminary Report and Written Opinion dated Jul. 21, 2015, PCT/US2014/011829, 10 pages.
International Preliminary Report and Written Opinion dated Sep. 15, 2015, PCT/US2014/021756, 8 pages.
International Preliminary Report and Written Opinion dated Feb. 8, 2016, PCT/US2015/049765, 19 pages.
International Preliminary Report and Written Opinion dated Mar. 23, 2017, PCT/US2015/049765, 13 pages.
Bell, "The polymerase chain reaction," Immunology Today, vol. 10, No. 10, (1989), pp. 351-355.
Lee, "Ligase Chain Reaction," The International Association of Biological Stanodardization, (1996), No. 24, pp. 197-199.
Communication Pursued to Article 94(3) EPC dated Sep. 18, 2017 in European Patent Application No. 14 706 709.4, 6 pages.
U.S. Appl. No. 13/370,874, filed Feb. 10, 2014 by John S. Oliver., Final Office action dated Aug. 28, 2018.
U.S. Appl. No. 14/852,086, filed Sep. 11, 2015 by Jeffrey H. Stokes et al., Final Office action dated Oct. 10, 2018.
Communication Pursued to Article 94(3) EPC dated May 23, 2018 in European Patent Application No. 14 706 709.4, 5 pages.
Gardner, et al., "Acyclic and dideoxy terminator preferences denote divergent sugar recognition by archaeon and Taq DNA polymerases," Nucleic Acids Research, (2002) vol. 30, No. 2, pp. 605-613.
Hammer, "Human Hybrids," Scientific American, May 2013, pp. 66-71.
Hirano, et al., ATP-dependent aggregation of single-stranded DNA by a bacterial SMC homodimer,: Then EMBO Journal, (1998), vol. 17, No. 23, pp. 7139-7148.
Lee, et al., "DNA sequencing with dye-labeled terminators and T7 DNA polymerase: effect of dyes and dNTPs on incorporation of dye-terminators and probability analysis of termination fragments," Nucleic Acids Research, (1992) vol. 20, No. 10, pp. 2471-2483.
Madiraju, et al., "Evidence for ATP Binding and Double-Stranded DNA Binding by *Escherichia coli* RecF Protein" Journal of Bacteriology, Dec. 1992, vol. 174, No. 23, pp. 7705-7710.
Norais, et al., "DdrB Protein, an Alternative Deinococcus radiodurans SSB Induced by Ionizing Radiation," Journal of Biological Chemistry, Aug. 7, 2009, vol. 284, No. 32, pp. 21402-21412.
Palanichelvam, et al., "The capsid protein of tomato yellow leaf curl virus binds cooperatively to single-stranded DNA," Journal of General Virology, (1998) vol. 79, pp. 2829-2833.
Thorslund., et al., "The Breast cancer tumor suppressor BRCA2 promotes the specific targeting of RAD51 to single-stranded DNA," Nature Structural & Molecular Biology, Oct. 2010, vol. 17, No. 10, pp. 12631265.
U.S. Appl. No. 14/852,086, filed Sep. 11, 2015 by Jeffrey H. Stokes et al., Final Office action dated Aug. 29, 2017.
U.S. Appl. No. 14/105,391, filed Dec. 13, 2013 by Valentin Dimitrov, Notice of Allowance dated Sep. 27, 2017.
U.S. Appl. No. 13/370,874, filed Feb. 10, 2014 by John S. Oliver., Non-Final Office action dated Nov. 12, 2017.
U.S. Appl. No. 14/199,434, filed Mar. 6, 2014 by John S. Oliver, Notice of Allowance dated May 19, 2016.
U.S. Appl. No. 14/331,629, filed Jul. 15, 2014 by John Oliver, Non-Final Office action dated Sep. 15, 2016.
U.S. Appl. No. 13/370,874, filed Feb. 20, 2012 by John S. Oliver, Non-Final Office action dated Feb. 23, 2017.
U.S. Appl. No. 14/852,086, filed Sep. 11, 2015 by Jeffrey H. Stokes et al., Non-Final Office action dated Feb. 15, 2017.
U.S. Appl. No. 14/105,391, filed Dec. 13, 2013 by Valentin Dimotrov, Non-Final Office action dated Mar. 31, 2017.
U.S. Appl. No. 12/732,870, filed Mar. 26, 2010 by John S. Oliver, Decision on Appela by the Patent Trial and Appeal Board (PTAB) dated Jun. 9, 2017.
U.S. Appl. No. 14/331,629, filed Feb. 15, 2014 by John S. Oliver, Notice of Allowance dated May 30, 2017.
U.S. Appl. No. 14/468,959, filed Aug. 26, 2014 by Peter Goldstein, Notice of Allowance dated Mar. 24, 2017.
U.S. Appl. No. 14/188,119, filed Mar. 5, 2014 by John S. Oliver, Notice of Allowance dated Jan. 5, 2017.
U.S. Appl. No. 13/370,874, filed Feb. 10, 2014 by John S. Oliver, Non-Final Office action dated Feb. 23, 2017.
U.S. Appl. No. 14/200,601, filed Mar. 7, 2014 by Stan Rose, Non-Final Office action dated Jun. 16, 2017.
U.S. Appl. No. 11/538,189, filed Oct. 3, 2006 by Xinsheng Ling et al., Final Office action dated Mar. 11, 2015.
U.S. Appl. No. 14/157,136, filed Jan. 16, 2014 by John S. Oliver, Non-Final Office action dated Sep. 30, 2015.
U.S. Appl. No. 14/036,509, filed Sep. 25, 2013 by John S. Oliver, Non-Final Office action dated Sep. 15, 2015.
U.S. Appl. No. 14/200,601, filed Mar. 7, 2014 by Stan Rose, Non-Final Office action dated Jan. 4, 2016.
U.S. Appl. No. 14/852,086, filed Sep. 11, 2015 by Jeffrey H. Stokes et al.
U.S. Appl. No. 14/157,136, filed Jan. 16, 2014, Non-Final Office action dated Jun. 16, 2016.
U.S. Appl. No. 14/036,509, filed Sep. 25, 2013 by John S. Oliver et al., Non-Final Office action dated Feb. 25, 2016.
U.S. Appl. No. 14/468,959, filed Aug. 26, 2014, first Office action dated Jul. 21, 2016.
U.S. Appl. No. 14/200,601, filed Mar. 7, 2014, by Stan Rose, Non-Final Office action dated Aug. 9, 2016.
U.S. Appl. No. 14/105,391, filed Dec. 13, 2013, by Valentin Dimotrov, Final Office Action dated Nov. 14, 2016.

\* cited by examiner

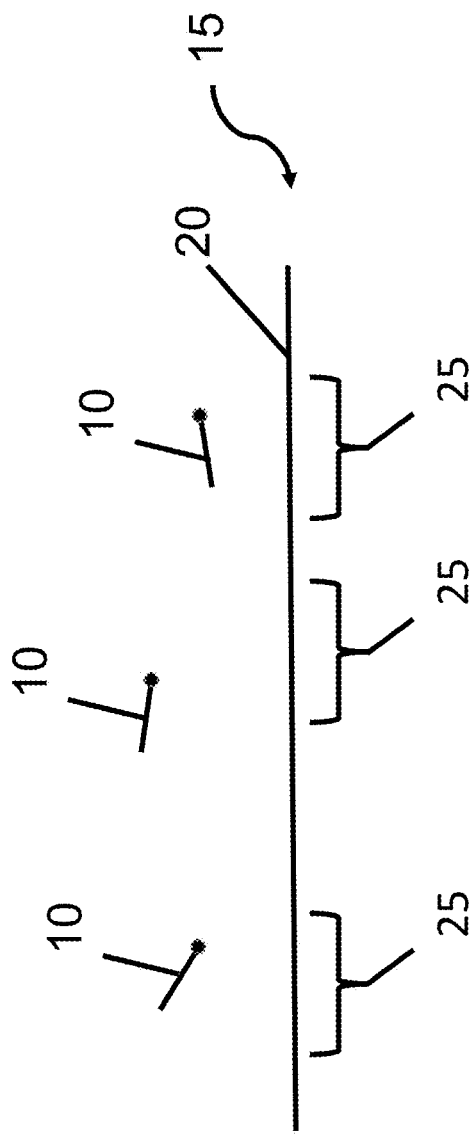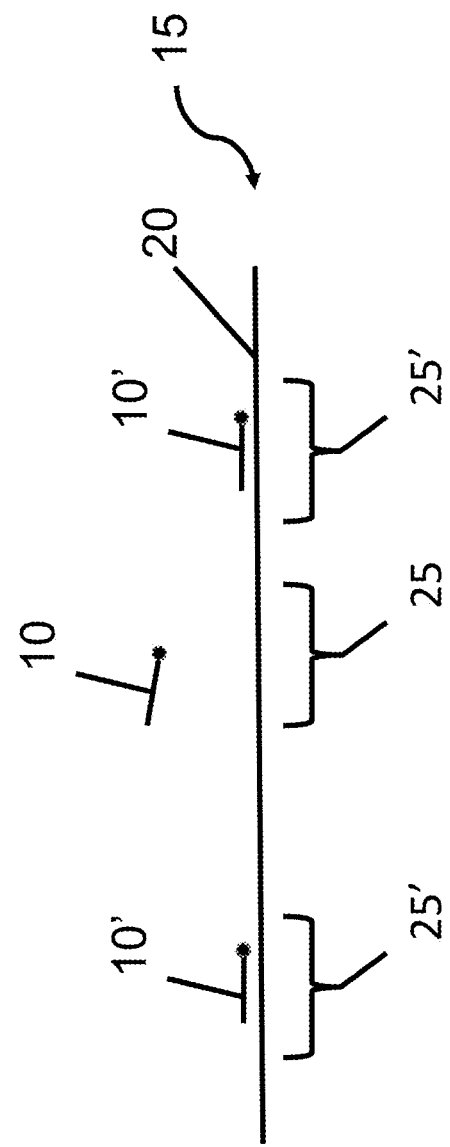

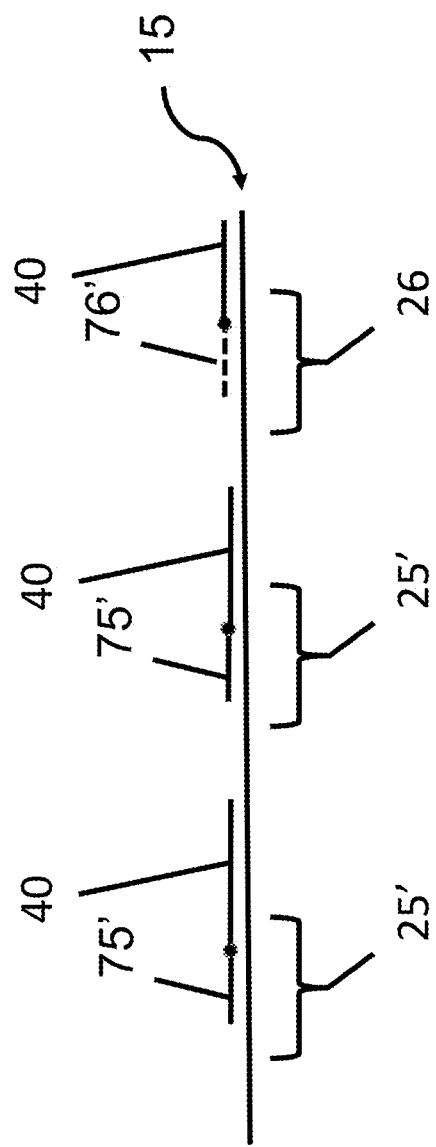

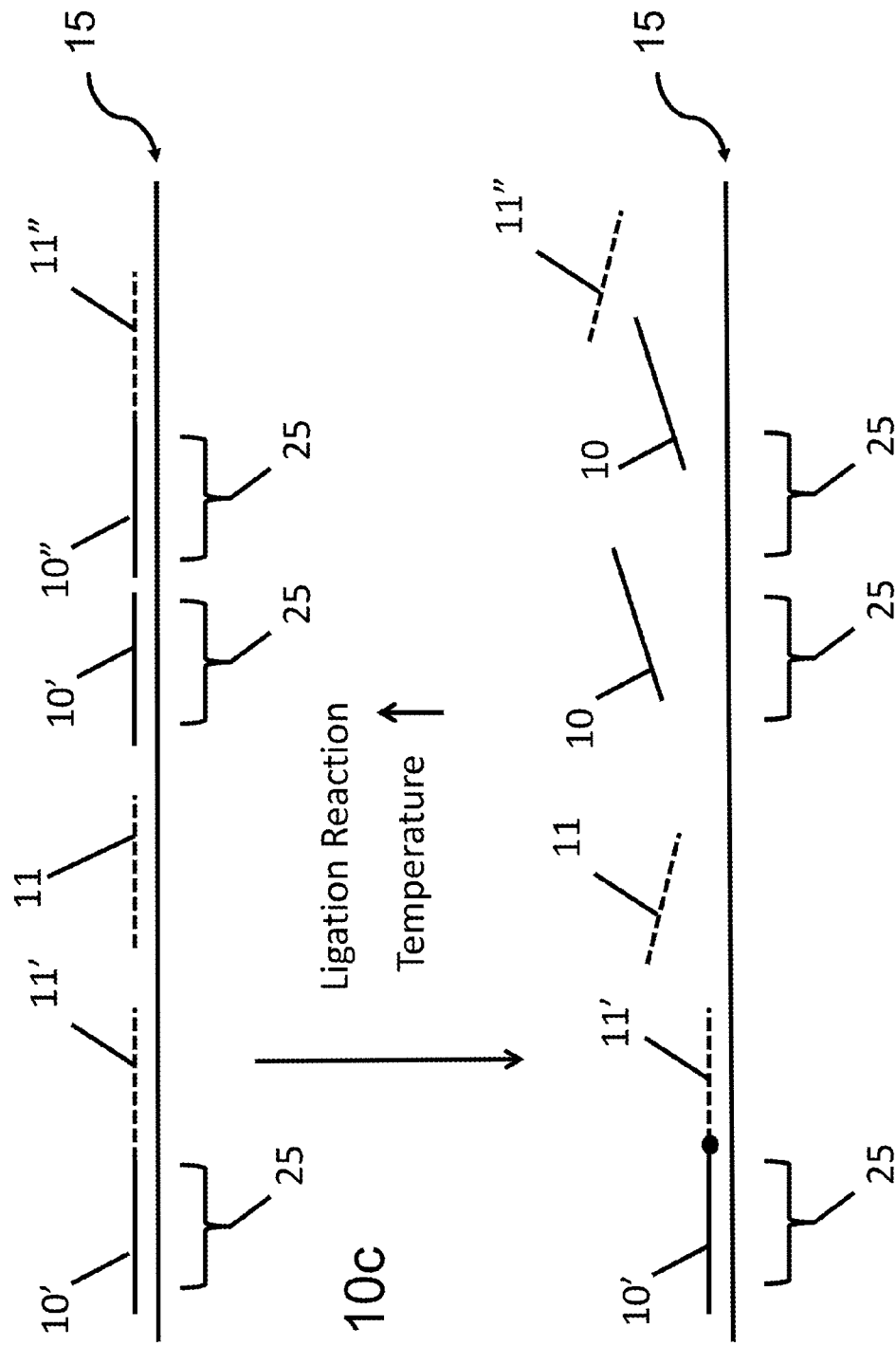

ENHANCED PROBE BINDING

CROSS REFERENCE TO RELATED APPLICATION

This application claims the benefit of priority under 35 U.S.C. § 119(e) to U.S. Provisional Patent Application Ser. No. 61/754,258 filed Jan. 18, 2013, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 25, 2014, is named NAB-013_SL.txt and is 1,344 bytes in size.

FIELD OF INVENTION

The present invention relates generally to methods for enhancing the binding of oligonucleotide probes to DNA and RNA samples for analysis. Mapping and sequencing of the DNA and RNA samples are contemplated herein.

BACKGROUND

A number of different approaches for sequencing nucleic acids exist. The traditional methods are the dideoxy-chain termination method described by Sanger et al., Proc Natl. Acad. Sci. USA, (1977) 74: 5463-67 and the chemical degradation method described by Maxam et al., Proc. Natl. Acad. Sci. USA, (1977) 74: 560-564. Of these two methods, the Sanger procedure has been the most widely used. The original Sanger method relied on radioactive labeling of the reaction products and separation of the reaction products by slab gel electrophoresis.

Both the Sanger and Maxam methods are time- and labor-intensive. The start of the Human Genome Project was the impetus for the development of improved, automated systems to perform Sanger sequencing. As a result, detection of fluorescence has replaced autoradiography and capillary electrophoresis has replaced the ultrathin slab gels originally used to separate reaction products. Automated sequencers have been developed and are capable of processing large numbers of samples without operator intervention.

The completion of the Human Genome Project has refocused the need for new technologies that are capable of rapidly and inexpensively determining the sequence of human and other genomes. There is has been much discussion in recent years about personalized medicine. The vision of personalized medicine involves every individual having his or her complete genome sequenced at high accuracy and using this information to guide clinical care, specifically for risk stratification of patients and pharmacogenomics.

In recent years, a number of technological advances have been developed enabling a great reduction in the cost of sequencing and substantially increasing the amount of sequence data produced. Most sequencing methods currently available utilize optical detection for the determination of the DNA sequence. The most prevalent sequencing methods are referred to as sequencing by synthesis (SBS).

SBS typically consists of the stepwise synthesis of a strand of DNA that is complementary to a template sequence from the target genome to be sequenced. The SBS methods can be divided into those that are performed in batch mode and those that are performed in real-time. The batch mode processes rely on the stepwise synthesis of the new DNA strand with the limitation that the synthesis is only allowed to proceed for one nucleotide position, for one nucleotide type, or for the combination of one nucleotide position and one nucleotide type. The incorporation of the nucleotide occurs in parallel for large numbers of templates. Detection is achieved using a variety of methods.

The batch mode processes utilizing a single nucleotide type are used by Roche for pyrosequencing with the 454 platform. The Roche technology (see, e.g., Margulies et al. (2005) Nature, 437:376-380; U.S. Pat. Nos. 6,274,320; 6,258,568; 6,210,891) utilizes pyrosequencing. The method depends on several enzymes and cofactors to produce luminescence when a nucleotide is incorporated. A single nucleotide species is introduced into a large number of small reaction vessels each containing multiple copies of a single template. The incorporation of the nucleotide is accompanied by light emission. When the reaction has run to completion, the reagents are washed from the reaction volumes and a next nucleotide and its required reagents are washed into the reactions. Each template is thus extended in an iterative fashion, one nucleotide at a time. Multiple incorporations of the same nucleotide require the quantitative determination of the amount of light emitted. Homopolymer tracts in templates may be difficult to accurately sequence as the incremental amount of light emitted for each subsequent position in the homopolymer becomes small compared to the total amount emitted.

In other variations of the SBS method, platforms by Helicos (see, e.g., Quake et al Proc. Nat. Acad. Sci. USA (2003) 100: 3960-3964; U.S. Pat. Nos. 6,818,395; 6,911,345; 7,297,518; 7,462,449 and 7,501,245), Illumina (see, e.g., Bennett et al. Pharmacogenomics (2005) 6:373-382), and Intelligent Bio-Systems (see, e.g., Ju et al. Proc. Nat. Acad. Sci. USA (2006) 103:19635-19640) allow only the incorporation of a single nucleotide at each step. Template strands are attached to a solid support and a primer sequence is annealed. A polymerase is used to extend the primer to make a complement to the template. The nucleotides are derivatized such that after the incorporation of a single nucleotide, the growing strand is incapable of further extension. The nucleotides are further derivatized to make them fluorescent. In the Helicos technology, the four nucleotides are labeled with the same fluorescent tag. This requires that each nucleotide type be added separately. In contrast, the Illumina and Intelligent Bio-Systems technologies utilize four different fluorescent tags so that a mixture of all four derivatized nucleotides may be added at the same time. For both technologies, the incorporation of a nucleotide is accompanied by the appearance of fluorescence in the growing strand. In the case of Illumina, the wavelength of the fluorescence emission indicates the identity of the newly incorporated nucleotide. In the Helicos technology, only a single nucleotide type is added at each cycle. Thus, the appearance of fluorescence at a position on the solid support indicates the incorporation of the added nucleotide for that template. Templates that do not incorporate the nucleotide present in the reaction remain dark.

Following the observation of any incorporated fluorescence, the blocking groups and fluorescent tags are removed prior to the next cycle. Multiple cycles result in the acquisition of sequence data for many templates in a single run. The instrumentation typical for these technologies is said to allow for the automated acquisition of sequence information for hundreds of thousands to millions of templates in parallel.

SBS methods may also be performed in real-time. In particular, polymerase is used to incorporate fluorescently labeled nucleotides and the fluorescence is observed during DNA strand synthesis. The four nucleotides are labeled with different fluorescent tags. The fluorescent tags are attached to the terminal phosphate of the nucleotide triphosphate. During incorporation of the nucleotide into the growing strand the fluorophore is released to solution and the growing strand remains non-fluorescent. The identity of the incorporated strand is determined while the nucleotide resides in the active site of the enzyme and before the cleaved diphosphate is released to bulk solution.

The fluorescence of the incorporated nucleotide typically is measured in the presence of a background fluorescence from a much larger concentration of unincorporated nucleotide. Pacific Biosciences (see, e.g., U.S. Pat. Nos. 7,170,050; 7,302,146; 7,315,019; 7,476,503; and 7,476,504) identifies the incorporated nucleotide based on the residence time in the polymerase active site. Fluorescence emission from the active site for an appropriate time indicates incorporation and the emission wavelength determines the identity of the incorporated nucleotide. Polymerase is attached to the bottom of zero-mode waveguides. Zero-mode waveguides are reaction cells whose dimensions limit the passage of light from the excitation sources. Thus, only fluorescent tags close to the bottom surface of the reaction volume are excited.

Other recently developed methods to sequence DNA rely on hybridization and ligation. Both the SOLiD and Complete Genomics technologies rely on the combination of hybridization and ligation. The SOLiD system (Life Technologies) immobilizes short template strands via an adapter. A primer and a pool of labeled oligonucleotides containing two fixed positions and six degenerate positions is hybridized to the template. The primer hybridizes to the adaptor. Each pool consists of 16,384 different sequences. Four fluorescent dyes are used to label the oligonucleotides in a pool in a fashion that creates four subsets from the sixteen combinations at the two fixed positions. Thus, each fluorescent tag is associated with four of the sixteen possible combinations. Following hybridization, a ligase is added and any probes in the pool that hybridized contiguously with the primer are ligated to the primer. The fluorescence of the hybridized and ligated product is determined. The fluorescence defines which subset of sequences hybridized to the template and ligated to the primer. The terminal three bases and the associated fluorescent tag are cleaved from the hybridized and ligated oligonucleotide. Subsequent rounds of another round of hybridization, ligation, and cleavage are performed. In this first series of reactions, each cycle identifies a subset for the pair of nucleotides in the template that is 5 nucleotides downstream from subset of pairs that were identified in the last cycle. After several cycles, the primer, and the oligonucleotides that have been ligated to it, is washed off the template.

The entire procedure is repeated starting with a primer that is one nucleotide shorter than the original primer, then with primers that are two, three, and four nucleotides shorter than the original primer. These subsequent rounds shift the frame of interrogation so that the bases that make-up the template strand can be identified from the union between the two subsets of reaction that overlapped at that position.

Complete Genomics technology utilizes a similar hybridization and ligation method (see, e.g., US Patent Application Publication Nos. 20080234136; 20090005252; 20090011943; and 20090176652). In the Complete Genomics technology, a primer is hybridized to an adaptor that is attached to the end of the template. A series of pools of oligonucleotides is constructed. In each pool, the nucleotide at a single position is identified by using four-color fluorescence. The remaining positions are degenerate. The first pool is hybridized to the template. Oligonucleotides that hybridize adjacent to the primer are subsequently ligated. After washing excess oligonucleotides away, the fluorescence of the ligated oligonucleotide identifies the nucleotide at the defined position in that pool. The ligated primer and oligonucleotide are washed off the template and the process is repeated with the next pool of oligonucleotides that probe the next position down from the primer.

The SBS and hybridization-ligation methods generate short pieces or reads of DNA sequence. While the short reads can be used to re-sequence human genomes, they are not favorable for the de novo assembly of human genomes. With the recent realization that human genomes contain large numbers of inversions, translocations, duplications, and indels (e.g., mutations that include both insertions, deletions, and the combination thereof), the quality of human genome data from short reads is even more suspect. Genetic rearrangements are even more prevalent in cancer.

While short read technology methods that incorporate paired-end reads have been proposed and the length of the sequence data from these technologies has increased incrementally over the last two years, it is clear that longer read technologies are necessary for the accurate assembly of human genome data.

In addition to the undesirable nature of short reads, all of the DNA sequencing methods described above employ optical detection. The throughput of optical methods limits the ultimate performance characteristics of any of these sequencing technologies. Optical methods are capable of identifying single molecules. However, the time required to observe and accurately identify events is typically too slow to meet the need for higher throughput. While the current generation of sequencing technologies has lowered the cost of sequencing by orders of magnitude in comparison to the methods used to sequence the first human genomes, the methods remain too slow, costly, and inaccurate for routine analysis of human genomes.

In methods employing oligonucleotide probes, it is recognized that probe binding is subject to both false negatives and false positives. In the case of false negatives, not every region on the analyte that is complementary to a probe necessarily has a probe bound thereto at a given temperature, T. Likewise, in the case of false positives, probes bind to regions of the analyte that are not identically complementary, i.e., regions where, for example, there may be a single base mismatch. In both of these instances, errors may be produced in the final map or sequence data.

SUMMARY

A need exists for efficient methods and devices capable of rapid and accurate nucleic acid sequencing for de novo assembly of human genomes. It is desirable to have long read lengths and to use as little nucleic acid template as possible. Moreover, single-molecule optical detection of DNA has limitations with respect to sensitivity and therefore speed. Thus, there remains a need for improved methods and devices for the analysis of biopolymers, including methods and devices for mapping and sequencing such biopolymers. A need also exists for improved methods by which probes are bound to samples to be analyzed to thereby reduce the occurrence of false positive and false negative probe binding.

The embodiments of the invention provide assay methods for preparing analyte samples for mapping and sequencing using nanopore, microchannel or nanochannel analysis devices.

Embodiments of the present invention relate broadly to the recognition and use of thermodynamic effects and kinetic effects to improve binding of oligonucleotide probes to DNA and RNA sample analytes. These effects may be used to reduce both false negatives that result from probes failing to bind at complementary sites on the analyte as well false positives resulting from probes binding at sites having complementary mismatches. Improvements in probe binding provide enhanced accuracy when using the probes to derive maps and sequences of the samples being analyzed.

More particularly, in one aspect, embodiments of the invention relate to a method for preparing a biomolecule analyte which includes the steps of providing a single-stranded DNA or RNA template, hybridizing a plurality of identical, sequence-specific oligonucleotide probes to the template, conducting a base extension reaction from a 3' end of a hybridized probe, terminating the base-extension reaction, and allowing additional unhybridized probes from the plurality of probes to hybridize to the template.

One or more of the following features may be included. The base extension reaction may be allowed to produce a double-stranded retion on the single-stranded template of a length approximating the resolution of a detection apparatus. The base extension reaction and the termination may carried out simultaneously. Following termination of the base extension reaction, the analyte may be maintained at a temperature for a time sufficient to melt probe mismatches, e.g., sufficient to melt substantially all probe mismatches. This process may be carried out one or more times. The probes may be provided with tags, such as double stranded DNA, gold beads, quantum dots, or fluorophores. A at least a portion of the template or probes may be provided with a protein coating, e.g., RecA, T4 gene 32 protein, f1 gene V protein, human replication protein A, Pf3 single-stranded binding protein, adenovirus DNA binding protein, or *E. coli* single-stranded binding protein.

The single-stranded DNA or RNA template may include one or more secondary structures. In such cases, the secondary structure may be denatured following termination of any of the base extension reactions. In particular, in another aspect of the invention, a method for preparing a biomolecule analyte includes providing a single-stranded DNA or RNA template comprising one or more secondary structures. A plurality of identical, sequence-specific oligonucleotide probes is hybridized to the template. A base extension reaction is conducted from a 3' end of a hybridized probe, The base-extension reaction is terminated. The template is denatured to break at least a portion of said one or more secondary structures. The base extension reaction, termination, and denaturing steps are then repeated at least one additional time with a different plurality of identical, sequence-specific oligonucleotide probes to prepare the biomolecule analyte.

One or more of the following features may be included. The denaturing step may include heating. At least a portion of the probes may include tagged probes. At least a portion of the template or probes may be coated with a protein. The base extension reaction and the termination may be carried out simultaneously.

In some embodiments of the invention, two or more probes may be used. In another aspect, embodiments of the invention include a method for preparing a biomolecule analyte, the method including providing a single-stranded DNA or RNA template, providing a first plurality of identical, sequence-specific oligonucleotide probes having a first melting temperature, and a second plurality of identical, sequence-specific oligonucleotide probes having a second melting temperature, the first melting temperature being higher than the second melting temperature. The first plurality of probes has a different sequence than the second plurality of probes. The probes from the first plurality are hybridized to the template at a temperature approximately equal to or below the first melting temperature, and a first base-extension reaction is conducted from a 3' end of a hybridized first probe. The first base extension-reaction is terminated and then additional unhybridized probes from the first plurality of probes are allowed to hybridize to the template. A second base-extension reaction is then conducted from a 3' end of a hybridized probe from the first plurality of probes and is terminated. Finally, probes from the second plurality of identical, sequence-specific oligonucleotide probes are hybridized to the template at a temperature approximately equal to or below the second melting temperature.

One or more of the following features may be included. At least a portion of the probes may include tagged probes. At least a portion of the template or probes may be coated with a protein. The first base extension reaction and its termination may be carried out simultaneously. The second base extension reaction and its termination may be carried out simultaneously.

Optionally, a third base-extension reaction may be conducted to extend from a 3' end of a hybridized probe from the second plurality of probes. This is followed by termination of the base extension reaction and allowing additional unhybridized probes from the second plurality of probes to hybridize to the template. The third base extension reaction and its termination may be carried out simultaneously.

Additional base extension reactions may be allowed as desired. For example, a fourth base-extension reaction may be conducted in the at least one single-stranded region from a 3' end of a hybridized probe from the second plurality of probes, and then terminated. The fourth base-extension reaction and its termination may be carried out simultaneously.

In some embodiments of the invention, an enzymatic ligation may be substituted for the base extension reaction. Accordingly, in yet another aspect, embodiments of the invention include a method for preparing a biomolecule analyte by providing a single-stranded DNA or RNA template. A first plurality of identical, sequence-specific oligonucleotide probes and a second plurality of identical oligonucleotide probes are provided, The first plurality of probes and the second plurality of probes are hybridized to the template. An enzymatic ligation reaction is conducted to ligate hybridized probes to an adjacent probe from the second plurality of identical oligonucleotide probes, terminating the ligation reaction, and allowing additional unhybridized probes from the first plurality of probes to hybridize to the template.

One or more of the following features may be included. The probes from the second plurality may each include one degenerate or universal site. At least a portion of the first plurality of probes and/or second plurality of probes may include tagged probes. At least a portion of the template and/or first plurality of probes and/or second plurality of probes may be coated with a protein.

The biomolecule analytes prepared by the methods described herein may be used to map or sequence biomolecules using nanopores or fluidic channels such as nanochannels and microchannels. For example, any of the biomolecule analytes prepared by the disclosed methods may be analyzed as follows. An apparatus may be provided, the apparatus having a first fluid chamber, a second fluid chamber, a membrane positioned between the first and second chambers and a nanopore extending through the membrane such that the first and second chambers are in fluid communication via the nanopore. The biomolecule analyte may be introduced into the first chamber and translocated from the first chamber through the nanopore and into the second chamber. Changes in an electrical property across the nanopore may be monitored as the biomolecule analyte is translocated therethrough, the changes in the electrical property corresponding to locations along the biomolecule analyte containing probes. The changes in the electrical property as a function of time may be recorded.

Moreover, any of the biomolecule analytes prepared by the disclosed methods may be analyzed as follows. The biomolecule analyte may be disposed in a fluidic nanochannel or microchannel. A potential may be applied along the fluidic channel. The biomolecule analyte may be translocated from a first end of the fluidic channel to a second end of the fluidic channel. Electrical properties may be detected as the biomolecule analyte moves through the fluidic channel, the electrical properties corresponding to at least one detector volume in the fluidic channel, each detector volume being defined by two or more sensing electrodes disposed along the length of the fluidic channel, with the detected electrical signals indicating locations of hybridized probes along the biomolecule analyte.

BRIEF DESCRIPTION OF THE FIGURES

FIGS. 6a-6d are schematic depictions of an assay preparation method in accordance with an embodiment of the invention in which oligonucleotide probes are hybridized to a single-stranded DNA or RNA template, a base extension reaction is carried out, and a subsequent hybridization of remaining unbound probes is allowed to proceed.

FIGS. 9a-9g are schematic depictions of an assay preparation method in accordance with an embodiment of the invention in which two different oligonucleotide probes are employed. In this embodiment, a first probe set is hybridized to a single-stranded DNA or RNA template using the methods of embodiments of the invention, and then a second probe set is hybridized to the analyte.

FIGS. 10a-10d are schematic depictions of an assay preparation method in accordance with an embodiment of the invention in which ligation is used to enhance hybridization of probes to an analyte. FIG. 10a discloses "ANNNCGAGACT" as SEQ ID NO: 1 and "AGTCTCGNNNT" as SEQ ID NO: 4. FIG. 10b discloses "ANNNCGAGACT" as SEQ ID NO: 1.

FIG. 11b is a schematic depiction of an assay method in accordance with an embodiment of the invention showing a current measurement waveform as a DNA molecule having a tagged probe translocates through the nanopore apparatus of FIG. 11a.

DETAILED DESCRIPTION

Figure 1:
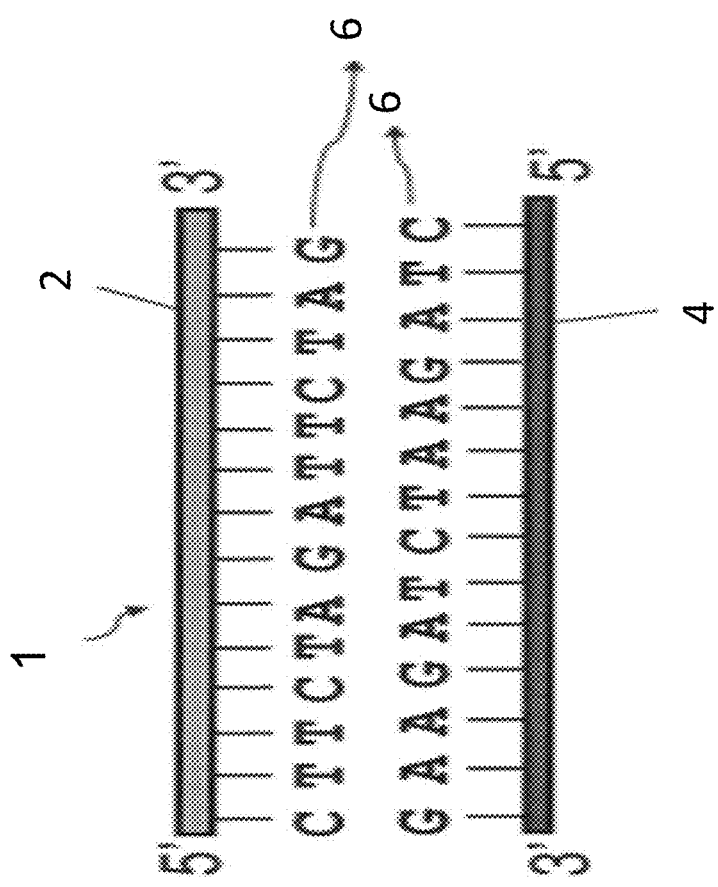
FIG. 1 is a schematic depiction of a DNA molecule (SEQ ID NO: 2).

Embodiments of the present relate generally to methods for enhancing the binding of oligonucleotide probes to DNA and RNA samples for analysis.

As used in this description and the accompanying claims, the following terms shall have the meanings given, unless the context indicates otherwise:

A "template" or "target" means a biomolecule, for example, having sequence information that is to be determined using embodiments of the present invention. The target or template may be a biomolecule such as deoxyribonucleic acid, a ribonucleic acid, a protein, or a polypeptide. The target or template may be single-stranded or double-stranded.

A "probe" means any molecule or assembly of molecules capable of sequence-specific covalent or non-covalent binding to a template. Accordingly, a sequence-specific probe is capable of binding to a portion of the template having a complementary sequence.

A "biomolecule analyte" is any molecule or assembly of molecules, e.g., a template having probes bound thereto, that is to be analyzed. An exemplary biomolecule analyte may include a single-stranded DNA or RNA template, with one or more sequence-specific oligonucleotide probes hybridized to a corresponding complementary portion of the template; a binding moiety may coat at least a portion of the single-stranded DNA or RNA template and/or probes.

A "tag" means a moiety that is attached to a probe in order to make the probe more visible to a detector. These tags may be proteins, double-stranded DNA, single-stranded DNA, dendrimers, particles, or other molecules.

A "false negative" means that not every region on the analyte that is complementary to a probe necessarily has a probe bound thereto at a given temperature, T.

A "false positive" means a probe that has bound to a region of the analyte that is not identically complementary, i.e., a region where, for example, there may be a single base mismatch.

In one embodiment, a biomolecule of interest is hybridized with the entire library of probes of a given length. For example, the biomolecule of interest can be hybridized with the entire universe of 4096 (i.e., $4^6$) possible six-mers. The hybridization can be done sequentially (i.e., one probe after another) or in parallel (i.e., a plurality of biomolecules of interest are each separately hybridized simultaneously with each of the possible probes.) Alternatively, the probes can be separated from each other in both space and time. Additionally, more than one probe type may be hybridized to the same biomolecule of interest at the same time.

The set of probes used to perform sequencing may be a subset of the complete library of probes of a given length, such as about 85%, 75%, 65%, 55%, 45%, or 33% of the library. For instance, if sequencing is performed on a biomolecule that starts as double-stranded DNA, then only one-half of the probes that make up a library may be needed. Other subsets of the library may be designed to allow sequencing as well. If some information concerning the target sequence is known prior to performing the sequencing reaction, it may be possible to use a small subset of the total library. For instance, if the sequencing reaction is being performed to determine if single nucleotide polymorphisms are present with respect to a reference sequence, then a small number of probes with respect to the complete library may be used. Alternatively, the set of probes may not all be the same length. In an embodiment, a set of at least two probes may be used for hybridization, rather than an entire library of probes or subset thereof. In another embodiment, probes may be separated by (GC) content or other determinants of probe binding strength, in order to allow for optimization of reaction conditions. By separating the probes based on relative properties, multiple probes may be incorporated into a single hybridization reaction. Further, the probes may be grouped based on their related optimum reaction environment preferences. In yet another embodiment, pools of probes may be simultaneously hybridized to a biomolecule of interest. A pool of probes is a group of probes of different composition, each of which may likely be present in many copies. The composition of the probes may be chosen so as to reduce the chance of competitive binding to the biomolecule of interest. Alternatively, the composition of multiple pools may be chosen so that the same competitive binding is not present in all pools occupied by a single probe.

It should be understood that the methods of embodiments of the present invention are not intended to be limited solely to sequencing. As such, embodiments of the invention can be used to provide accurate maps of analytes. In particular, rather than employing a library of probes as described above, in mapping applications, one or more sets of sequence-specific probes can be used to map, with high accuracy, the specific location of regions on the analyte which are complementary to such probes.

In still another embodiment, the probes may include tags, thereby enhancing detection as the hybridized probes translocate through the sequencing system. In addition, different tags may be used to help distinguish among the different probes. These tags may be proteins, double-stranded DNA, single-stranded DNA, particles, or other molecules.

It should be understood that embodiments of the invention are not intended to be limited strictly to DNA and RNA oligonucleotide probes. Rather, it is envisioned that oligonucleotide analog probes such as those comprising LNAs, PNAs, 2'-methoxy nucleotide analogs, or other analogs may be used as well.

Figure 2:
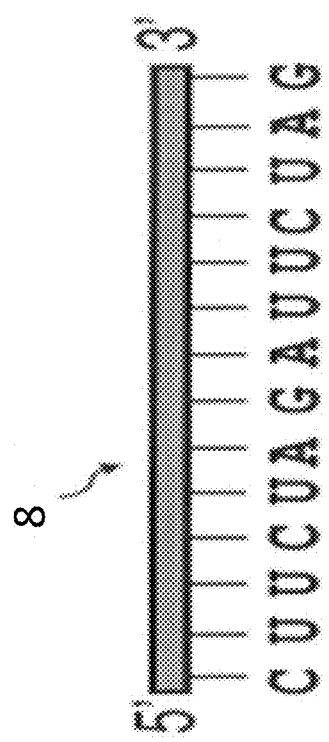
FIG. 2 is a schematic depiction of an RNA molecule (SEQ ID NO: 3).

In one embodiment, the process of sequencing a biomolecule such as single strands of DNA or RNA using one or more probes may performed as follows. Suitable processes are also described in U.S. Ser. No. 11/538,189, published as U.S. Publication No. 2007/0190542, incorporated by reference herein in its entirety. Referring to FIG. 1, a DNA molecule 1 is schematically depicted and is structured in two strands 2, 4 positioned in anti-parallel relation to one another. Each of the two opposing strands 2, 4 may be sequentially formed from repeating groups of nucleotides 6 where each nucleotide 6 consists of a phosphate group, 2-deoxyribose sugar and one of four nitrogen-containing bases. The nitrogen-containing bases include cytosine (C), adenine (A), guanine (G) and thymine (T). DNA strands 2, 4 are read in a particular direction, from the top (called the 5' or "five prime" end) to the bottom (called the 3' or "three prime" end). Similarly, RNA molecules 8, as schematically depicted in FIG. 2, are polynucleotide chains, which differ from those of DNA 1 by having ribose sugar instead of deoxyribose and uracil bases (U) instead of thymine bases (T).

Traditionally, in determining the particular arrangement of the bases 6 and thereby the sequences of the molecules, a process called hybridization may be utilized. The hybridization process is the association, or binding, of two genetic sequences with one another. This process is predictable because the bases 6 in the molecules do not share an equal affinity for one another. T (or U) bases favor binding with A bases while C bases favor binding with G bases. Binding is mediated via hydrogen bonds that exist between the opposing base pairs. For example, A binds to T (or U) using two hydrogen bonds, while C binds to G using three hydrogen bonds.

Figure 3:
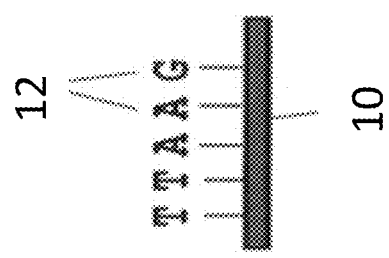
FIG. 3 is a schematic depiction of a hybridizing oligonucleotide probe.

A hybridizing oligonucleotide, i.e., a probe, may be used to determine and identify the sequence of bases in the molecule of interest. FIG. 3 illustrates a probe 10 that is a short DNA sequence having a known composition. Probes 10 may be of any length depending on the number of bases 12 that they include. For example, a probe 10 that includes six bases 12 is referred to as a six-mer probe wherein each of the six bases 12 in the probe 10 may be any one of the known four natural base types A, T(U), C or G. Alternately, the probe may include non-natural bases.

In this regard, the total number of unique probes 10 in a library is dependent upon the number of bases 12 contained within each probe 10 and the number of different types of bases in the probes. If only the four natural bases are used in probe 10, the total number of probes in the library is determined by the formula $4^n$ (four raised to the n power) where n is equal to the total number of bases 12 in each probe 10. Formulas for other arrangements or types of bases are well known in the art. Accordingly, the size of the probe library can be expressed as $4^n$-mer probes 10. For the purpose of illustration, in the context of a six-mer probe, the total number of possible unique, identifiable probe combinations includes $4^6$ (four raised to the sixth power) or 4096 unique six-mer probes 10. The inclusion of non-natural bases allows for the creation of probes that have spaces or wildcards therein in a manner that expands the versatility of the library, while reducing the number of probes that may be needed to reach the final sequence result. Probes that include universal bases organized into patterns with natural bases may also be used, for example those described in U.S. Pat. Nos. 7,071,324, 7,034,143, and 6,689,563, which are incorporated herein by reference in their entireties.

Figure 4:
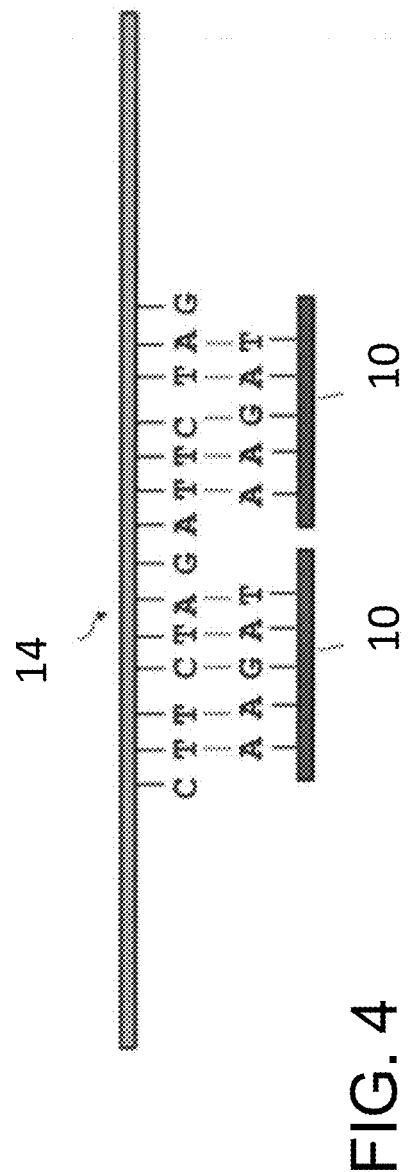
FIG. 4 is a schematic depiction of a single-stranded DNA molecule (SEQ ID NO: 2) hybridized with two identical probes.

The process of hybridization using probes 10, as depicted in FIG. 4, may begin by denaturing a double-stranded biomolecule, or by starting with a single-stranded biomolecule. Denaturing is accomplished usually through the application of heat or chemicals, such that the hydrogen bonds between adjacent strands of the biomolecule are broken. The term "melting" may be used interchangeably with the term "denaturing".

The hydrogen bonds between the two halves of an original double-stranded DNA may be broken, leaving two single strands of DNA whose bases are now available for hydrogen bonding. After the biomolecule 14 has been denatured, a single-stranded probe 10 may be introduced to the biomolecule 14 to locate portions of the biomolecule 14 that have a base sequence that correlates in a complementary manner to the sequence that is found in the probe 10. In order to hybridize the biomolecule 14 with the probe 10, the denatured biomolecule 14 and a plurality of the probes 10 having a known sequence are both introduced into a solution. The solution may be an ionic solution, such as a salt-containing solution. The mixture may be mixed to facilitate binding of the probes 10 to the biomolecule 14 strand along portions thereof that have a matched complementary sequence. Hybridization of the biomolecule 14 using the probe 10 may be accomplished before the biomolecule 14 is introduced into a nanopore sequencing apparatus or after the denatured biomolecule 14 has been placed into the cis chamber of such an apparatus. In this case, after the denatured biomolecule has been added to the cis chamber, buffer solution containing probes 10 with a known sequence is also added to the cis chamber and allowed to hybridize with the biomolecule 14 before the hybridized biomolecule is translocated.

Probes are typically relatively short, e.g., 4-8 bases, and bind in a fully complementary manner to templates. Nevertheless, in methods employing oligonucleotide probes, it is recognized that probe binding is subject to both false negative and false positives. In the case of false negatives, not every region on the analyte that is complementary to a probe necessarily has a probe bound thereto at a given temperature, T. Likewise, in the case of false positives, probes occasionally bind to regions of the analyte that are not identically complementary, i.e., regions where, for example, there may be a single base or multiple base mismatch. In each of these instances, errors may be produced in the final map or sequence data.

Embodiments of the present invention are based upon the recognition that both thermodynamic effects and kinetic effects may be used to enhance probe binding to an analyte and to reduce false negatives and false positives. For example, false positives may be reduced by inducing probes bound with one or more base mismatches to become unbound by, e.g., controlling the temperature of the reaction.

Figure 5:
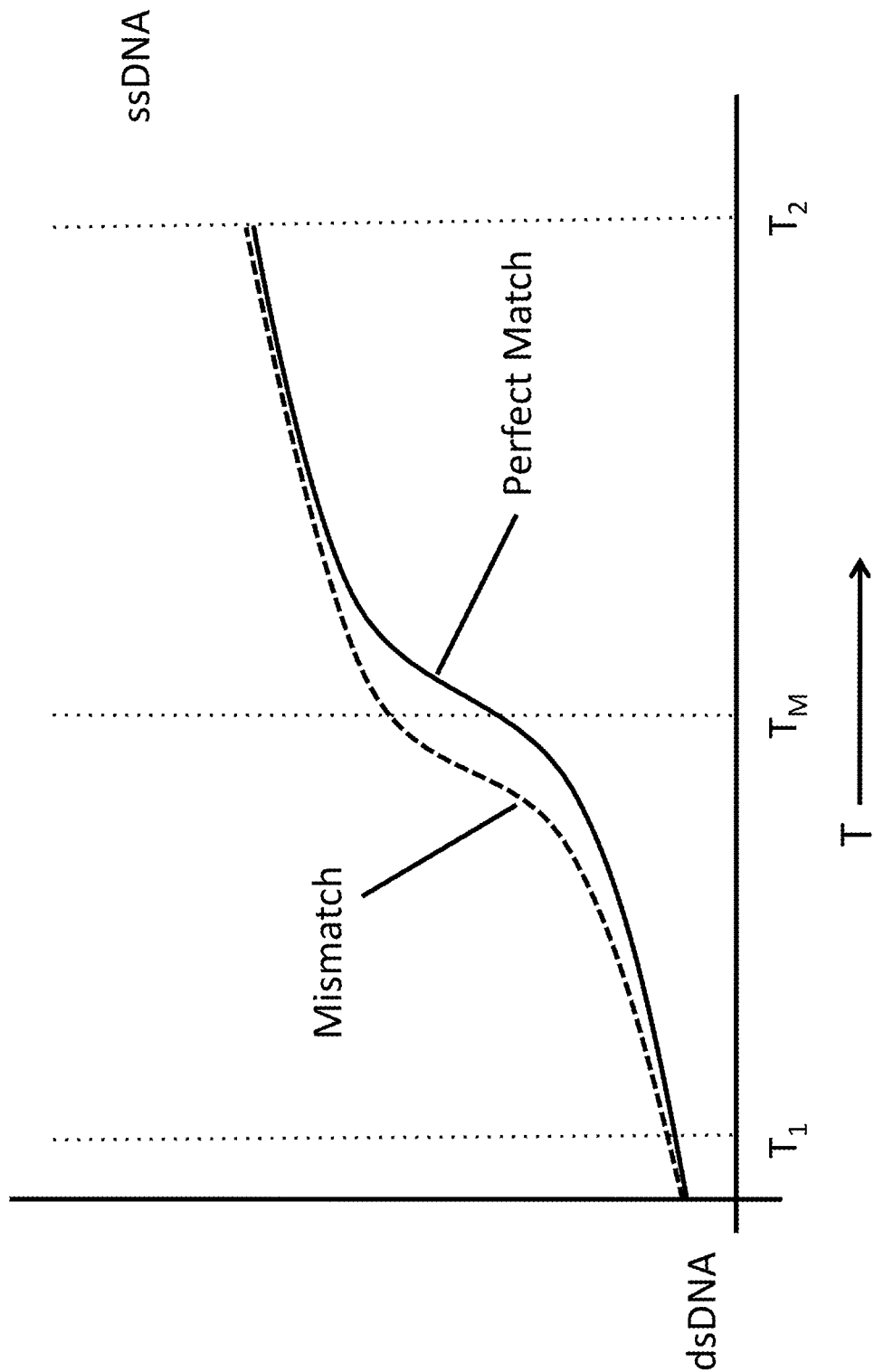
FIG. 5 is a schematic representation of a melting curve showing the relative amounts of double-stranded DNA versus single-stranded DNA over a range of temperatures.

A melting curve for DNA is depicted schematically in FIG. 5. In that Figure, it can be seen that at a temperature $T_1$ double-stranded DNA (dsDNA) remains in its double-stranded configuration. At a higher temperature, $T_2$, the strand has become completely denatured into two single-stranded DNA (ssDNA) templates. As applied to the binding of probes to ssDNA, this means that as reaction temperature increases, probe binding decreases. At a reaction temperature $T_M$ (the melting temperature) approximately half of all probes that can bind to the denatured analyte strand have done so.

Thus, as shown in FIG. 5, when the probing reaction is maintained at $T_1$, there is approximately a 100% chance that a probe will be bound at a complementary site. Likewise, at $T_2$, there is approximately a 0% chance of a bound probe. At $T_M$, there is approximately a 50% chance that a probe will be bound. The process of probe binding is dynamic. As such, this does not mean that a particular subset of the complementary sites on the analyte remain bound with probes and the others remain unbound; rather, because probes continuously become bound and unbound over time, it means that at any given complementary recognition site on the analyte, there is approximately a 50% chance that a probe will be bound at any given time. As a result of the foregoing, if one were to conduct a probing reaction at $T_M$, and then to run the resulting analyte in a sequencing apparatus, only about 50% of the possible sites complementary to the probe would be detected on each molecule, i.e., there would be approximately 50% false negatives on each molecule. However, each molecule would have a different collection of complementary sites bound. If a sufficient number of molecules are detected all of the complementary binding sites may be determined. However, it is desirable to reduce false negatives so that each molecule is bound at a large proportion of the complementary sites so that the identity of each molecule in a complex mixture may be determined with high accuracy.

As will be described in detail below, false negatives may be reduced through the use of a base extension reaction, such as a primer extension reaction, utilizing for example, a polymerase and one or more nucleotides. In such reactions, which form a nucleic acid complementary to a nucleic acid template, a primer complementary to a single-stranded DNA template is typically employed. Starting at the primer, a DNA polymerase may be used to add mononucleotides complementary to the template at the 3' end of the primer. Various base extension reactions will be familiar to those of ordinary skill in the art. Note that if the template comprises RNA, an RNA dependent DNA polymerase is employed.

One embodiment of the present invention relates to improved methods for the preparation of biomolecule analytes. In the embodiment, shown in FIGS. 6a-6d, a denatured biomolecule analyte 15 is formed from a single-stranded DNA (ssDNA) or RNA template 20 exposed to probes 10. The probes may be ssDNA, RNA or other modified nucleotides that selectively hybridize to the analyte. The template 20 is shown to include three regions 25, referred to herein as probe recognition sites, which are complementary to the probes 10 being used. As such, each of the regions 25 is a potential binding site for a probe 10. In this example, each probe 10 is a short, known ssDNA sequence. The probes 10 may be of any length depending on the number of bases that they include. Each of the probes is preferably of an identical sequence, thereby causing the probes to selectively hybridize only to probe recognition sites 25 of the biomolecule template 20 that have a complementary sequence. The template 20 and probes 10 are depicted prior to hybridization in FIG. 6a. For purposes of clarity in FIGS. 6a-6d, probes 10 are shown having a small dot at the 3' end. This dot is not intended to signify a physical structure; rather, it is included simply to designate the 3' end of the probe.

The biomolecule analyte 15 is shown in FIG. 6b following hybridization of probes to the biomolecule template. Note that as shown in FIG. 6b, two probes (designated 10') have become bound at two probe recognition sites (designated 25'), while one probe 10 and probe recognition site 25 remain unbound. Were one to analyze the analyte following this step, the unbound probe recognition site 25 would be read as a false negative.

Figure 6C:
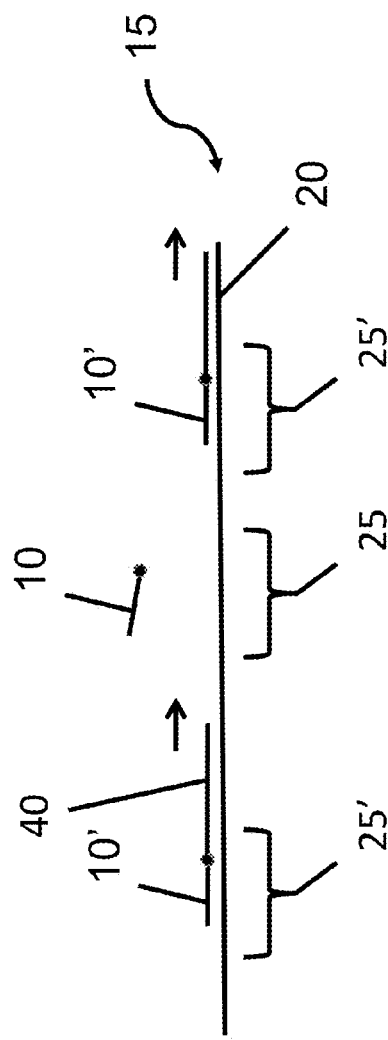

Following hybridization, a base extension reaction, such as a primer extension reaction, utilizing for example, a polymerase and one or more nucleotides, is performed as depicted in FIG. 6c. In such reactions, which form a nucleic acid complementary to a nucleic acid template, a primer complementary to a single-stranded DNA template is typically employed. In the present embodiment, each of the bound probes 10' may be used as a primer in the base extension reaction. The probes are extended from their 3' ends along the template 20 to create duplex regions 40. The base extension reaction causes the probes 10' to become more securely hybridized to the template.

It is preferred that the base extension reaction be limited in scope. If allowed to continue over extended lengths, the base extension may overwrite unbound probe recognition sites 25, rendering them as permanent false negatives. Instead, rather than extending a long distance from the 3' end of each probe, the base extension reaction may be terminated once the extensions have reached a length approximating the detection limits of the sequencing apparatus, such that the double-stranded region on the single-stranded template may have a length approximating the resolution of a detection apparatus. This leaves unbound probe recognition sites 25 unoccupied for subsequent probing reactions. Extension reactions may be terminated by the addition of dideoxy-nucleotides or other chain terminating nucleotides, such as 3'-amino-modified oligonucleotides, at a suitable time after the beginning of the extension reaction. Alternatively, the chain terminating nucleotides may be included with the cognate nucleotides in the extension reaction. Suitable adjustment of the concentrations of cognate and terminating nucleotides may be used to limit the extent of elongation during the extension reaction.

Figure 6D:
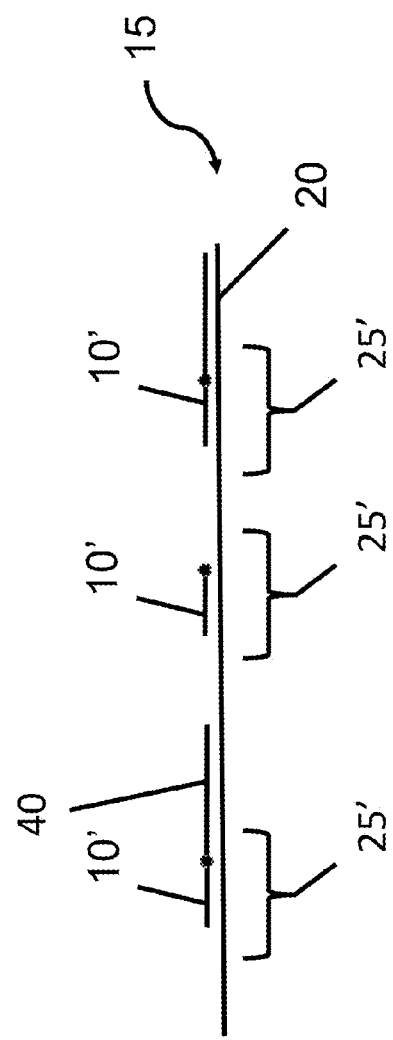

The extension of a subset of probes 10 to form duplex 40 irreversibly binds the probes to the template 20 under the reaction conditions and removes them from the equilibrium between probes and template. Following the base extension reaction, hybridization of remaining unbound probes 10, to unbound probe recognition sites 25, is allowed to proceed as depicted in FIG. 6d. Thus, over time, unbound probe recognition sites 25 will subsequently become bound probe recognition sites 25', thereby reducing the number of false negatives on the analyte. However, because the previously bound probes 10' acted as primers for the base extension reaction, they will have remained bound to the template. As such, it becomes possible to have substantially all probe recognition sites bound by complementary probes. It should be understood that the steps depicted in FIGS. 6a-6d are intended as a schematic presentation and may have multiple elements (e.g., extension and termination) occurring simultaneously.

For example, in a typical biomolecule analyte preparation, the single-stranded template may be combined with a sequence-specific oligonucleotide probe, a polymerase, each of the four nucleotides used to synthesize DNA, (deoxyadeninetriphosphate, dATP; deoxycytidinetriphosphate, dCTP; deoxyguanosinetriphosphate, dGTP; and deoxy thymidinetriphosphate), as well as the dideoxy versions of each of those nucleotides (ddATP, ddCTP, ddGTP and ddTTP). Thus, when placed in the presence of the template and maintained at the melting temperature $T_M$ of the probe, at any given time, approximately 50% of the probes will be hybridized to the template. Likewise, if a temperature below $T_M$ of the probe is used, a higher percentage of probes will hybridize to the template. This partial hybridization is depicted in FIG. 6b. Among the hybridized probes, certain of them will act as primers for the polymerase, and base extension will begin. The ratio of the deoxy- to the dideoxy-forms of the nucleotide is used to regulate the length of the base extension, as the dideoxy-nucleotides terminate base extension reactions. Thus, if the ratio of deoxy-nucleotides to dideoxy-nucleotides is, for example, 100:1, it is expected that on average, base extensions will proceed for 100 bases prior to termination.

The extension reaction is preferably as short as possible, but sufficiently long to permanently anchor the probe to the template. In practice, an extension of 80 to 100 bases may be preferable. Moreover, preferably, the extension reaction should not extend for a distance longer than can be resolved by a detector, e.g., currently about 300 bases. The duration of the extension reaction, i.e., time before termination, depends on the polymerase used and the rate of incorporation of nucleotides. Termination of extension may be accomplished by removing polymerase, removing nucleotides, removing magnesium (preferably with ethylenediaminetetraacetic acid (EDTA)) to inactivate the polymerase, heat killing the polymerase, or by using mixtures of terminating and extending nucleotides.

The base extension is depicted in FIG. 6c. Probes that have served as primers for base extension reactions remain bound to the analyte. Over a period of time, additional unhybridized probes will become bound as shown in FIG. 6d and act as primers for additional base extension reactions. Thus, eventually most, if not all, probe recognition sites become hybridized with complementary probes, and false negatives are eliminated. In some embodiments, it may be desirable to add the probes in a step prior to adding the polymerase and the deoxy- and dideoxy-nucleotides.

While the method described with reference to FIGS. 6a-6d is useful in eliminating false negatives, it should be understood that the elimination of false positives is a further enhancement of embodiments of the present invention. False positives have previously been defined as instances where a probe has hybridized to a region of the analyte that is not identically complementary, i.e., a region where, for example, there may be a single base or multi-base mismatch. As shown in FIG. 5, probes having mismatches generally have a lower $T_M$ than probes having no mismatches.

The result of a lower $T_M$ for probes having mismatches means that, during the base extension described with respect to FIGS. 6a-6d, the analyte may be maintained at a temperature at or above the $T_M$ for a sufficient time, thereby causing mismatched probes to be denatured, i.e., melted, while extending correct hybridizations at complementary sites. By allowing the enzymatic extension to occur for longer times, false positives may be substantially reduced. The time and temperature may be sufficient to melt substantially all probe mismatches. In another embodiment of the invention, shown in FIGS. 8a-8d, the probes are provided with tags that serve to make the probes more visible to a detector. Thus, as described above, suitable tags include proteins, double-stranded DNA, single-stranded DNA, dendrimers, particles, or other molecules.

Figures 7A, 7B:
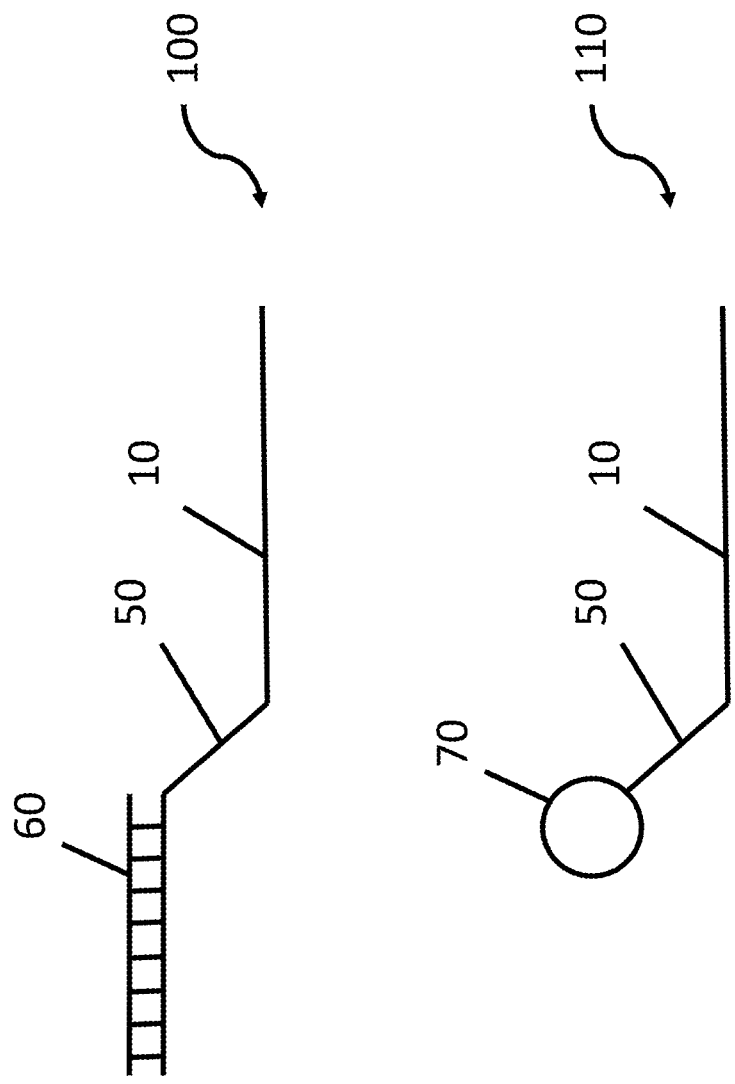
FIGS. 7a and 7b are schematic depictions of tagged probes useful in connection with embodiments of the present invention.

Examples of two tagged probes are provided in FIGS. 7a and 7b. In FIG. 7a, a tagged probe 100 includes a probe 10 having a sequence and a tag 60 connected to the 5' end of the probe sequence 10 by a linker 50. In the embodiment shown in FIG. 7a, the tag 60 may comprise a dsDNA segment, however, any of a wide variety of chemical/biological tags known to those skilled in the art may be employed. In FIG. 7b, a tagged probe 110 includes a probe 10 having a sequence and a tag 70 connected to the 5' end of the probe sequence 10 by a linker 50. In the embodiment shown in FIG. 7b, the tag 70 may comprise a gold bead, a quantum dot, a fluorophore, etc. The tags make electrical fluctuations in sequencing systems more noticeable as the hybridized probes translocate through such systems. In addition, different tags may be used to help distinguish among different probes.

Thus, the embodiment shown in FIGS. 8a-8d, is identical to that depicted in FIGS. 6a-6d except that tagged probes are used. Specifically, a denatured biomolecule analyte 15 is formed from a single-stranded DNA (ssDNA) or RNA template 20 exposed to tagged probes 100. The probes may be ssDNA, RNA or other modified nucleotides that selectively hybridize to the analyte. However, in this embodiment, the probes include a tag as described above. As before, the template 20 has been shown to include three probe recognition sites 25, which are complementary to the tagged probes 100 being used. The template 20 and tagged probes 100 are depicted prior to hybridization in FIG. 8a.

Figure 8A:
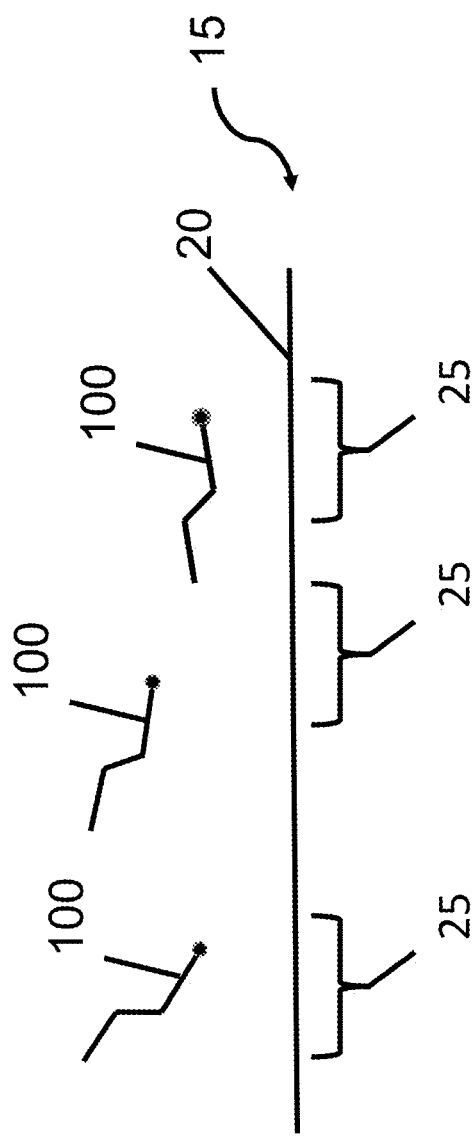
FIGS. 8a-8d are schematic depictions of an assay preparation method in accordance with an embodiment of the invention in which tagged oligonucleotide probes are hybridized to a single-stranded DNA or RNA template, a base extension reaction is carried out, and a subsequent hybridization of remaining unbound tagged probes is allowed to proceed.
Figure 8B:
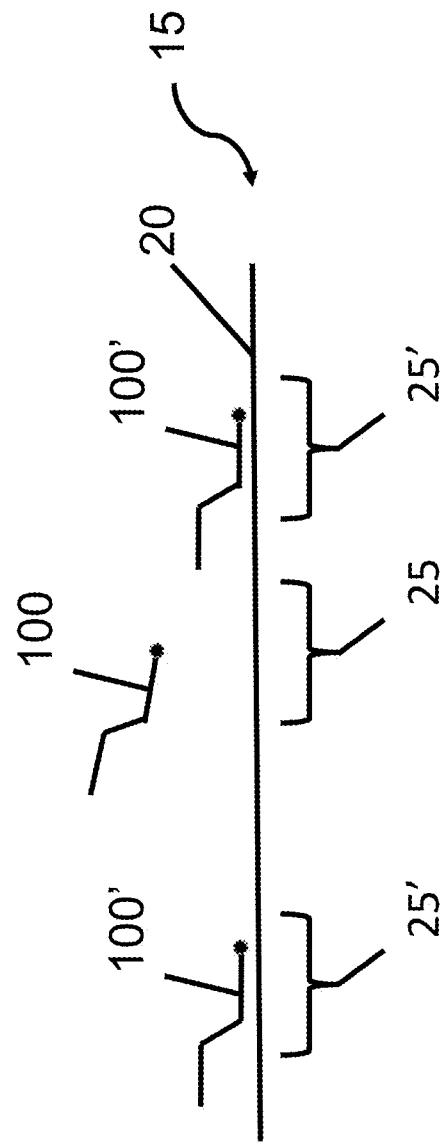

The biomolecule analyte 15 is shown in FIG. 8b following hybridization of tagged probes to the biomolecule template. Two tagged probes (designated 100') have become bound at two probe recognition sites (designated 25'), while one tagged probe 100 and probe recognition site 25 remain unbound.

Figure 8C:
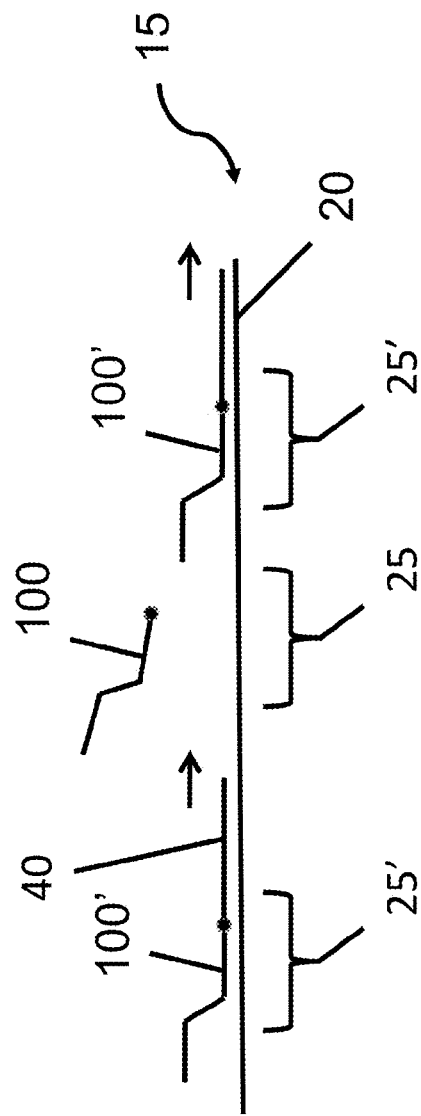

Following hybridization, a base extension reaction is performed as depicted in FIG. 8c. As before, each of the bound tagged probes 100' may be used as a primer in the base extension reaction. The probes are extended from their 3' ends along the template 20 to create duplex regions 40. Because they are attached to the 5' ends of the probes, the tags do not interfere with the base extension reaction.

Again, it is preferred that the base extension reaction be limited in scope. If allowed to continue over extended lengths, the base extension may overwrite unbound probe recognition sites 25, rendering them as permanent false negatives. Instead, rather than extending a long distance from the 3' end of each probe, the base extension reaction may be terminated once the extensions have reached a length approximating the detection limits of the sequencing apparatus. This leaves unbound probe recognition sites 25 unoccupied for subsequent probing reactions.

Figure 8D:
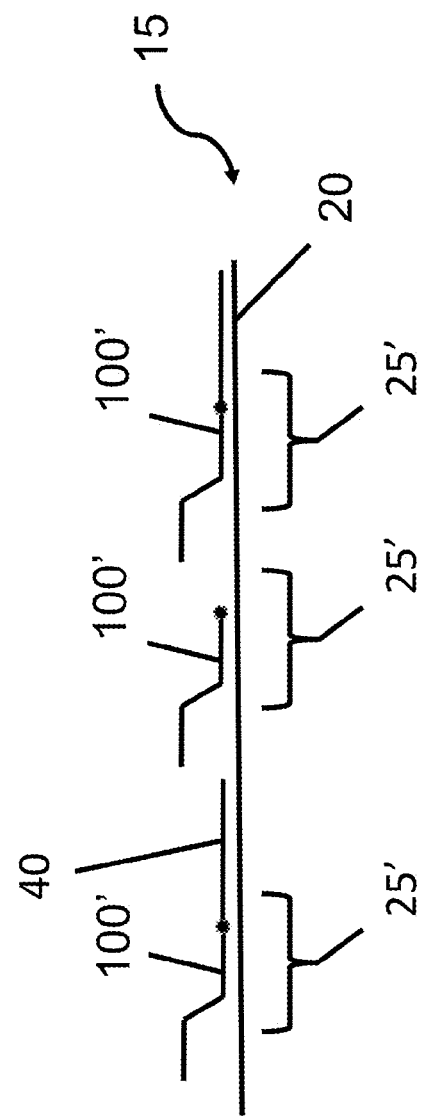

Following the base extension reaction, hybridization of remaining unbound probes 100, to unbound probe recognition sites 25, is allowed to proceed as depicted in FIG. 8d. As described previously, unbound probe recognition sites 25 will subsequently become bound probe recognition sites 25', thereby reducing the number of false negatives on the analyte. However, because the previously bound probes 100' acted as primers for the base extension reaction, they will have remained bound to the template. As such, it becomes possible to have substantially all probe recognition sites bound by complementary probes. As before, it should be understood that the steps depicted in FIGS. 8a-8d are intended as a schematic presentation and may have multiple elements occurring (e.g., extension and termination) simultaneously.

As such, the analyte may be combined with a tagged sequence-specific oligonucleotide probe, a polymerase, each of the four nucleotides used to synthesize DNA, and the dideoxy forms of each of those nucleotides. When placed in the presence of the analyte and maintained at $T_M$ for the tagged probe, at any given time, approximately 50% of the probes will hybridize. As discussed previously, a higher percentage of probes will hybridize if the hybridization reaction is carried out at a temperature below $T_M$ for the tagged probe. Partial hybridization is depicted in FIG. 8b. At least a portion of the tagged hybridized probes will act as primers for the polymerase, and base extension will begin as depicted in FIG. 8c. Tagged probes that have served as primers for base extension reactions remain bound to the analyte. Over a period of time, additional tagged probes will become bound and act as primers for additional base extension reactions as shown in FIG. 8d. Over time most, if not all, probe recognition sites become hybridized with complementary tagged probes, and false negatives are eliminated. As described previously, in some embodiments, it may be desirable to add the probes in a step prior to adding the polymerase and the deoxy- and dideoxy-nucleotides.

In a further embodiment of the invention, two or more pluralities of probes may be used. In the embodiment, shown in FIGS. 9a-9g, a denatured biomolecule analyte 15 is once again formed from a single-stranded DNA (ssDNA) or RNA template 20 exposed to a plurality of identical, sequence-specific oligonucleotide probes, i.e., a set of first probes 75 and a different plurality of identical, sequence-specific oligonucleotide probes, i.e., a set of second probes 76. The probes may be ssDNA, RNA or other modified nucleotides that selectively hybridize to the analyte. The probes of the first probe set 75 are identical to one another, and the probes of the second probe set 76 are also identical to one another, however the probes of the first set 75 are different than those of the second set 76. First probes 75 may have a melting temperature $T_{M1}$ which is higher than the melting temperature $T_{M2}$ of the second probes 76. The template 20 is shown to include two regions 25, referred to herein as first probe recognition sites, which are complementary to first probes 75 and one region 26, referred to herein as a second probe recognition site, which is complementary to second probes 76. As such, each of the regions 25 and 26 is a potential binding site for a probe.

Figure 9A:
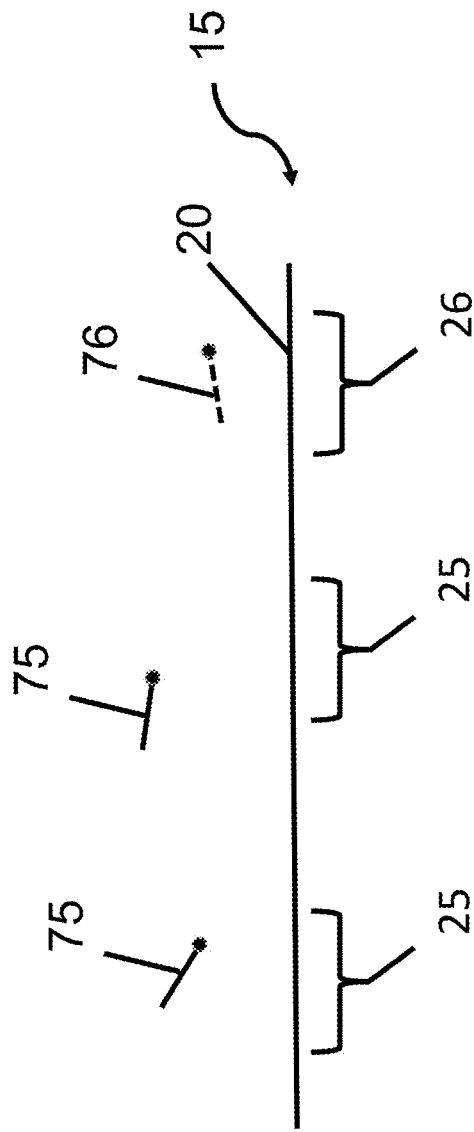

The template 20 and first and second probes 75, 76 are depicted prior to hybridization in FIG. 9a. As before, in FIGS. 9a-9g, probes are shown having a small dot at the 3' end. This dot is not intended to signify a physical structure; rather, it is included simply to designate the 3' end of the probe. Hybridization is preferably carried out at a temperature that is at or below $T_{M1}$, but above $T_{M2}$. Because $T_{M1}$ is higher than $T_{M2}$, the melting temperature of the second probe 76, the process conditions favor hybridization of the first probe 75.

Figure 9B:
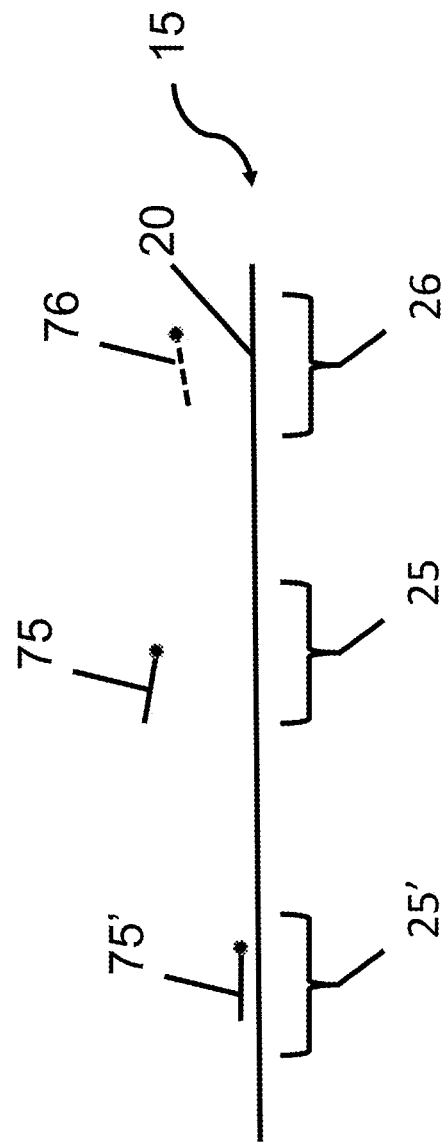

The biomolecule analyte 15 is shown in FIG. 9b once hybridization of probes to the biomolecule template has begun. Note that as shown in FIG. 9b, one first probe (designated 75') has become bound at a first probe recognition site (designated 25'), while one first probe 75 and first probe recognition site 25 remain unbound. Second probe 76 and second probe recognition site 26 also remain unbound.

Figure 9C:
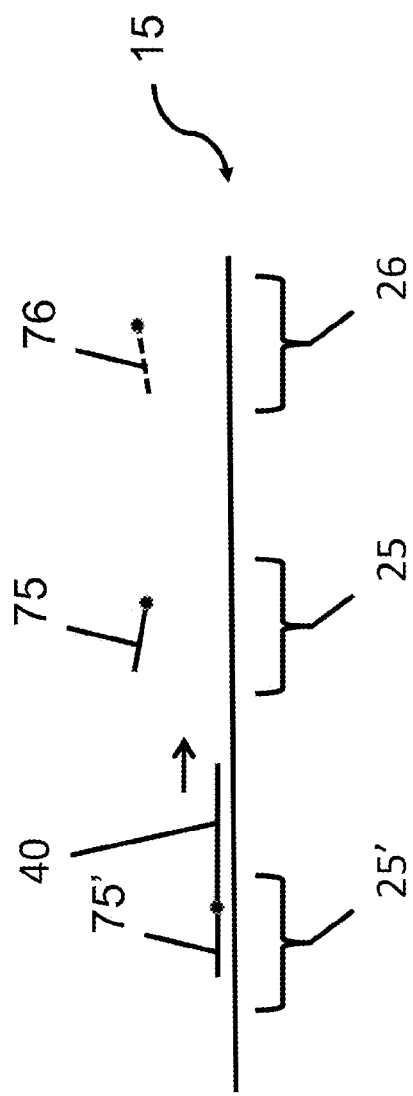

Following hybridization of the first probe, a base extension reaction off of the 3' end of first bound probe 75 is performed as depicted in FIG. 9c. The base extension 40 causes bound first probes 75' to become more securely hybridized to the template.

As before, it is preferred that the base extension reaction be limited in scope to prevent the extensions from overwriting unbound first 25 and second 26 probe recognition sites. This leaves unbound probe recognition sites unoccupied for subsequent probing reactions.

Figure 9D:
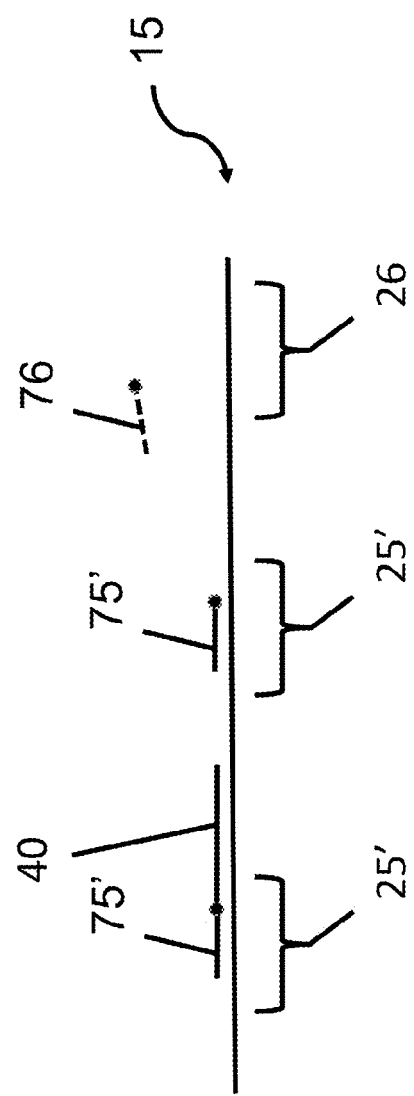

Following the base extension reaction, hybridization of remaining unbound first probes 75, to unbound first probe recognition sites 25, is allowed to proceed as depicted in FIG. 9d. Thus, over time, unbound first probe recognition sites 25 will subsequently become bound first probe recognition sites 25', thereby reducing the number of false negatives on the analyte. However, because the previously bound first probes 75' acted as primers for the base extension reaction, they will have remained bound to the template. As such, it becomes possible to have substantially all first probe recognition sites bound by complementary probes. Furthermore, since the temperature of the reaction is preferably higher than the melting temperature $T_{M2}$ of the second probes 76, binding of the first probes is favored over the second probes.

Figure 9E:
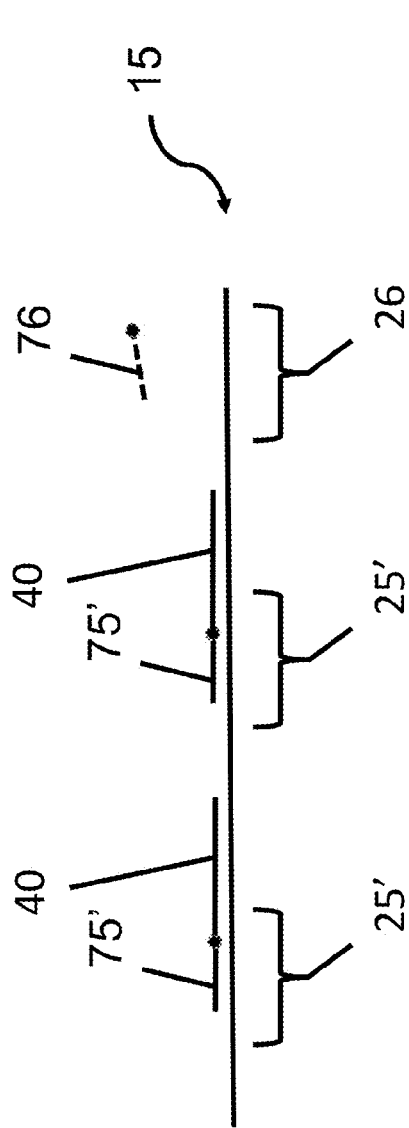

As additional first probes 75' are hybridized to additional first probe binding sites 25', base extension reactions from the newly hybridized first probes 75' take place as depicted in FIG. 9e.

Figure 9F:
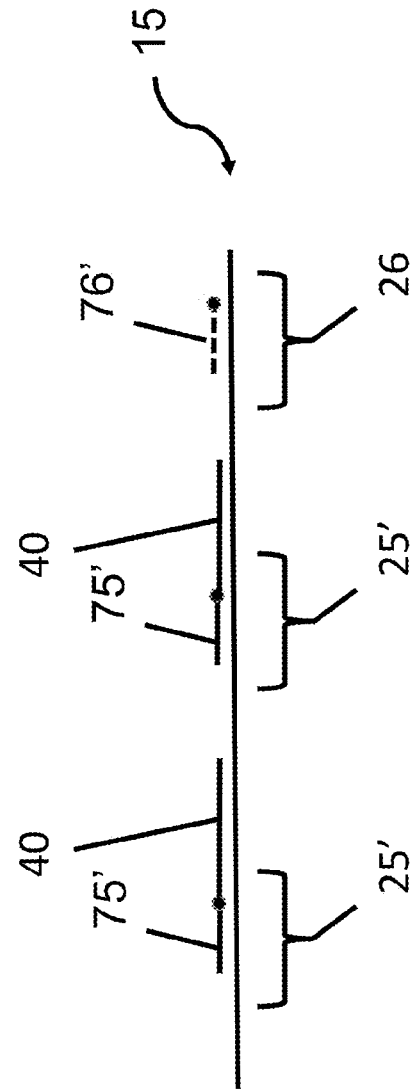

Once enough time has elapsed to allow substantially all first probes 75' to hybridize, the temperature is lowered to $T_{M2}$ or below and second probes 76 are allowed to hybridize to their complementary second probe binding sites 26. This is shown in FIG. 9f.

Following hybridization of the second probes 76' at second probe recognition sites 26', bound second probes 76' act as primers for a base extension reaction. This reaction, the result of which is depicted in FIG. 9g, serves the same purpose as before; namely, to prevent bound second probes 76' from melting from the second probe recognition site. Process conditions are maintained for a period of time sufficient to allow substantially all second probe recognition sites 26 to become bound by second probes 76.

It should be understood that the steps depicted in FIGS. 9a-9g are intended as a schematic presentation and may have multiple elements (e.g., extension and termination) occurring simultaneously. Although not depicted in FIGS. 9a-9g, it is to be further understood that either or both of the first 75 and second 76 probe sets may include detectable tags.

In another embodiment of the invention, rather than using a base extension reaction, a ligation reaction is carried out to secure probes to the analyte. The use of ligases to enhance probe binding is desirable in that ligases join probes with higher efficiency if the probes are perfectly complementary to the regions of the target analyte to which they are hybridized. As such, the use of ligases reduces enhanced binding of probes that contain mismatches with the analyte.

As used herein, the term "ligation" refers to a method of joining two or more nucleotides to one another. In general, the ligation methods described herein utilize enzymatic ligation using ligases. Such ligases include, but are not limited to DNA ligase I, DNA ligase II, DNA ligase III, DNA ligase IV, E. coli DNA ligase, T4 DNA ligase, T4 RNA ligase 2, T4 RNA ligase 2, T7 ligase, T3 DNA ligase, and thermostable ligases, including without limitation, Taq ligase and the like.

Figures 10A, 10B:
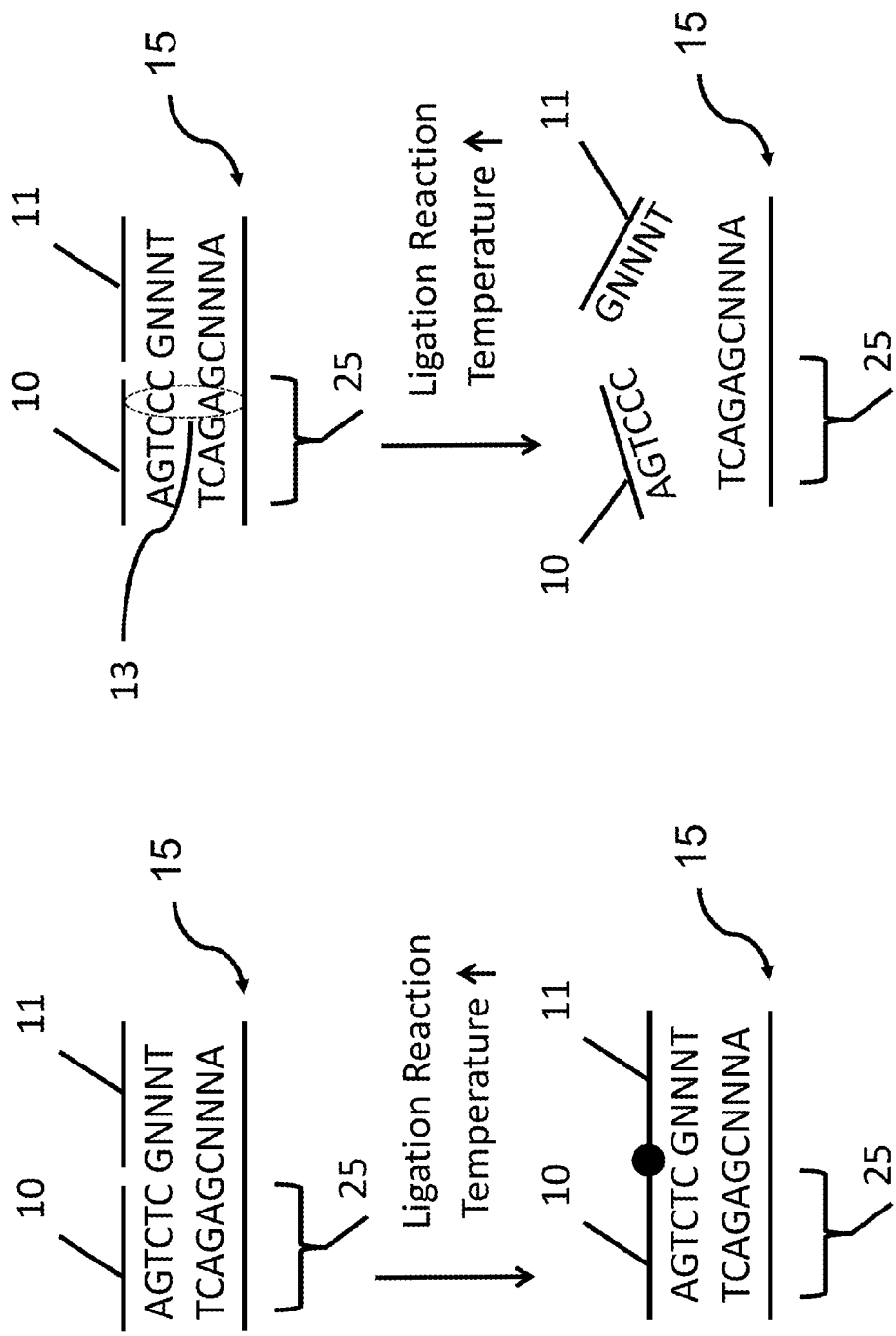

The relevance of ligases to the methods of embodiments of the present invention is illustrated schematically in FIGS. 10a-10b. In FIG. 10a, an 11-mer portion of the analyte 15 having the sequence TCAGAGCNNNA (SEQ ID NO: 1) is shown. A 6-mer probe 10 having the sequence AGTCTC is shown hybridized to its complementary probe recognition site 25, (i.e., the sequence TCAGAG). A 5-mer oligonucleotide probe 11, optionally having degenerate sites (N) is hybridized to the analyte immediately adjacent to the 3' end of the probe 10. It is noted that probe 11 need not include degenerate sites; rather it could be perfectly complementary or it could include universal bases which hybridize equally well with each of the four cognate bases. Since the probe 10 is perfectly complementary to the probe recognition site 25, when an enzymatic ligation is carried out, the 5-mer probe 11 becomes ligated to the probe 10, enhancing the ability of the probe to remain bound to the analyte even at temperatures above the melting temperature of the probe. (The ligation is represented in the Figure by a dot).

FIG. 10b also shows a probe 10 and a 5-mer oligonucleotide probe 11 hybridized to the analyte. Unlike FIG. 10a however, a mismatch 13 is present between the probe 10 and the probe recognition site 25. As a result, upon carrying out an enzymatic ligation reaction, probes 10 and 11 do not become ligated. Thus, the probe 10 receives no enhancement of its bond to the analyte and both probe 10 and the 5-mer probe 11 may be melted from the analyte. Consequently, it is seen that the use of the ligation reaction enhances the accuracy of the probes by enhancing bonding only of those probes that are perfectly matched to their corresponding probe recognition sites.

The use of the ligation reaction as applied to embodiments of the present invention is shown in FIGS. 10c and 10d. In FIG. 10c, the analyte 15 includes three probe recognition sites 25. Each of these is shown with a hybridized probe. Two of the probes 10' are perfectly complementary to their corresponding probe recognition sites, but one probe 10" includes a mismatch. Several 5-mer probes 11, of the type described with respect to FIG. 10a are hybridized as well. One of the probes 11' is directly adjacent to the 3' end of a perfectly hybridized probe 10', and one of the probes 11" is directly adjacent to the 3' end of a hybridized probe 10" having a mismatch.

Upon conducting an enzymatic ligation reaction, only the probe 10' that is perfectly complementary to its corresponding probe recognition site becomes ligated to the adjacent 5-mer probe 11'. Although 5-mer probe 11" is directly adjacent to the 3' end of bound probe 10", the existence of a mismatch in the probe 10" binding prevents probe 11" from ligating to probe 10". Thus, as shown in FIG. 10d, upon heating only the ligated probe 10' and probe 11' remain hybridized to the analyte. The mismatched probe 10" and its adjacent 5-mer probe 11" as well as other non-adjacent probes 10 and 11 are readily melted from the analyte.

The steps depicted in FIGS. 10a-10d are intended as a schematic presentation and may have multiple elements occurring simultaneously. It should be further understood that the description of probe 10 as a 6-mer oligonucleotide, and of probe 11 as a 5-mer oligonucleotide, are intended as examples for illustration purposes only. Probes may be of any length having utility in the applications described. Although not depicted in FIGS. 10a-10d, it is to be further understood that probes may include detectable tags.

In one embodiment of the invention, the incidence of false negative events resulting from secondary structure in the ssDNA or RNA template is reduced. Specifically, one reason for the inability of a probe to bind to a single-stranded DNA template, is the formation of secondary structure in that DNA template. A secondary structure is formed when a single-stranded molecule hybridizes to itself to form a hairpin, loop, etc. Secondary structures are generally undesirable in the methods disclosed herein, as they may appear to a detector as a hybridized probe. In addition, secondary structures may compete with the binding of the probe to a complementary site. Finally, secondary structures may promote clogging during translocation of templates or biomolecule analytes. The amount of false negative binding due to the secondary structure is determined by the relative stability of the probe bound structure as compared to that of the secondary structure. Thus, if the secondary structure has weak binding when the probe is tightly bound, very few false negative events are expected. However, if the secondary structure is very stable at the $T_M$ of the probe, then a high number of false negative binding events are expected because only a small proportion of the template are available for binding by probes.

It is preferred that the template DNA of the biomolecule analyte be hybridized with the probe under conditions such that some of the complementary sites involved in the formation of secondary structure are open. That is, conditions may be chosen to insure that the equilibrium of the secondary structure does not result in 100% of the template being in the form of the secondary structure. As such, portions of the ssDNA template that do not have secondary structure are available for binding by the probe. Thus, if the hybridization is conducted at the $T_M$ of the secondary structure, at any instant, 50% of the molecules have no secondary and are available for binding by the probe. The conditions may be selected such that the template DNA available for binding by the probe become completely bound or such that only a fraction of the available binding sites may be bound.

Structures in which the probe is hybridized to the template may be extended by a polymerase. As described above, it may be desirable to perform a limited extension of the probe. Following extension of bound probe, the template is heated in order to melt the secondary structure. The template may then be re-hybridized with the excess probe at the $T_M$ of the secondary structure. As before, the remaining single-stranded template is 50% available for binding by the probe. This cycle of hybridization, extension of probe, and denaturation may be repeated as many times as necessary to reduce the false negative rate resulting from the secondary structure. Temperatures or conditions other than the $T_M$ of the secondary structure may be used to perform the same conversions. Further, the conditions may be changed during each cycle of hybridization, extension, and denaturation.

In a further embodiment of the invention, the analyte, i.e., at least a portion of the template or probes, may be coated to enhance its ability to be detected. Coating methods are described in detail in co-pending US Patent Application Publication No. 20100243449, the teachings of which are incorporated by reference. Broadly, coated biomolecules typically have greater uniformity in their translocation rates, which leads to a decrease in positional error and thus more accurate sequencing. Due to its increased diameter, a coated biomolecule generally translocates through a sequencing system at a slower speed than a non-coated biomolecule. The translocation is preferably slow enough so that a signal can be detected during its passage from a first chamber into a second chamber. Exemplary binding moieties include proteins such as, for example, RecA, T4 gene 32 protein, f1 geneV protein, human replication protein A, Pf3 single-stranded binding protein, adenovirus DNA binding protein, and *E. coli* single-stranded binding protein.

The translocation rate or frequency may be further regulated by introducing a salt gradient between the chambers. Exemplary salt concentration ratios of the cis to the trans side of the chamber may include, but are not limited to, 1:2, 1:4, 1:6, and 1:8. For example, salt concentrations may range from about 0.5 M KCl to about 1M KCl on the cis side and from about 1M KCl to about 4M KCl on the trans side. The signal is preferably strong enough to be detected using known methods or methods described herein. Exemplary signal-to-noise ratios include, but are not limited to, 2:1, 5:1, 10:1, 15:1, 20:1, 50:1, 100:1, and 200:1. With a higher signal-to-noise ratio, a lower voltage may be used to effect translocation.

The analytes described herein may be configured for detection of positional information in a nanopore and/or a fluidic channel, i.e., a microchannel or nanochannel system. Mapping of analytes may be carried out using electrical detection methods employing nanopores, nanochannels or microchannels using the methods described in U.S. patent application Ser. No. 12/789,817, filed May 28, 2010, and issued as U.S. Pat. No. 8,246,799 B2 on Aug. 12, 2012, the teachings of which have previously been incorporated herein by reference. It is contemplated that such methods may be applied to analytes having either or both tagged and untagged probes.

Figure 11A:
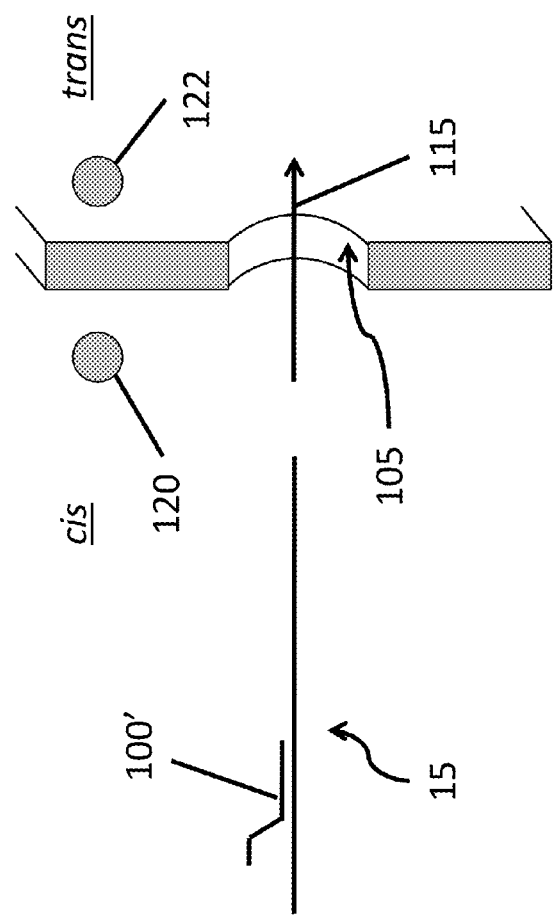
FIG. 11a is a schematic depiction of an assay method in accordance with an embodiment of the invention showing a DNA molecule having a tagged probe in a nanopore apparatus.

In one embodiment, current across a nanopore is measured during translocation of a DNA strand through the nanopore as shown in FIG. 11a. When used in embodiments of the present invention, a nanopore may have a diameter selected from a range of about 1 nm to about 1000 nm. More preferably the nanopore has a diameter that is between about 2.3 nm and about 100 nm. Even more preferably the nanopore has a diameter that is between about 2.3 nm and about 50 nm. Changes in an electrical property across a nanopore may be monitored as the analyte is translocated therethrough, with changes in the electrical property being used to distinguish regions of the analyte including probes, and regions of the analyte lacking probes.

Specifically, for nanopore 105, a measurable current 115 produced by electrodes 120, 122 runs parallel to the movement of the target analyte 15, i.e., a DNA molecule having a tagged probe 100'. Variations in current are a result of the relative diameter of the target analyte 15 as it passes through the nanopore 105. This relative increase in volume of the target analyte 15 passing through the nanopore 105 causes a temporary interruption or decrease in the current flow through the nanopore, resulting in a measurable current variation. Portions of the target analyte 15 including a tagged probe 100' are larger in diameter than portions of the target analyte that do not include a probe. As a result, when the tagged probe 100' passes through the nanopore 105, further interruptions or decreases in the current flow between electrodes 120, 122 occurs. These changes in current flow are depicted in the waveform 200 in FIG. 11b.

Figure 11B:
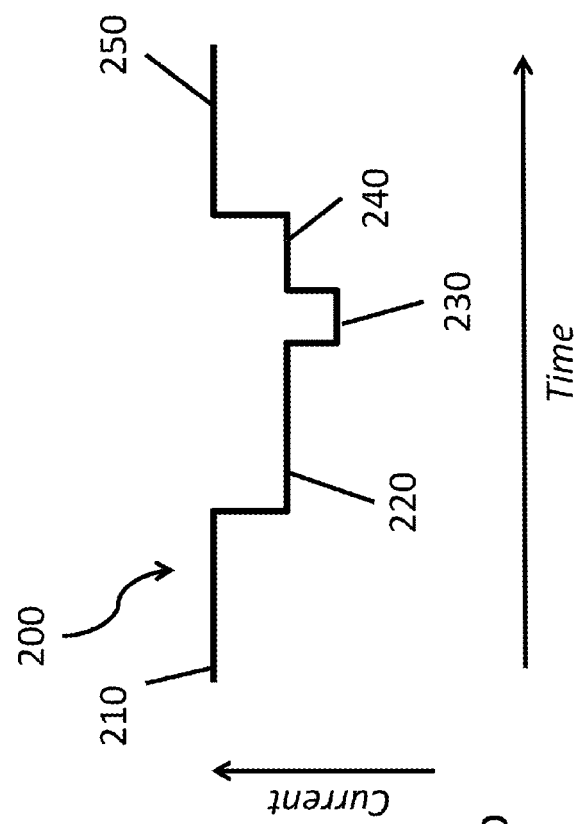

Analysis of the waveform 200 permits differentiation between regions of the analyte including probes and regions without probes, based, at least in part, on the detected changes in the electrical property, to thereby determine probe locations and map at least a portion of the double-stranded DNA template. In FIG. 11b, the waveform 200 depicts the changes in a detected electrical property as the analyte passes through the nanopore, and may be interpreted as follows. Current measurement 210 represents measured current prior to passage of the DNA molecule 15, i.e., the analyte, through the nanopore 105 from the cis side to the trans side. As the analyte enters the nanopore 105, from the cis side of the nanopore, the current is partially interrupted forming a first trough 220 in the recorded current. Once the probe 100' bound to the analyte enters the nanopore 105, a further decrease in current occurs, causing a deeper, second trough 230 in the current measurement. Upon passage of the probe 100' entirely through the nanopore 105, a distal portion of the analyte may remain in the nanopore. This causes the measured current 240 to rise to approximately the level of the first trough 220. Finally, once the entire analyte has passed completely through the nanopore 105 to the trans side, the measured current 250 returns to a level approximating that of the initial level 210. The current variation measurements are recorded as a function of time.

As a result, the periodic variations in current indicate where, as a function of relative or absolute position, the probes 100' have hybridized to complementary regions on the analyte 15. Since the probes are bound at probe recognition sites for the specific sequences of the probe, the relative or absolute position of the specific sequences associated with the recognition site for the particular probe employed may be determined. This allows mapping of those specific sequences on the analyte. Multiple maps produced using multiple probes may be generated.

The use of a binding moiety, such as the protein RecA, may further enhance detection of analytes and probe regions on analytes because the added bulk of the binding moiety coating causes greater current deflections.

Figure 12:
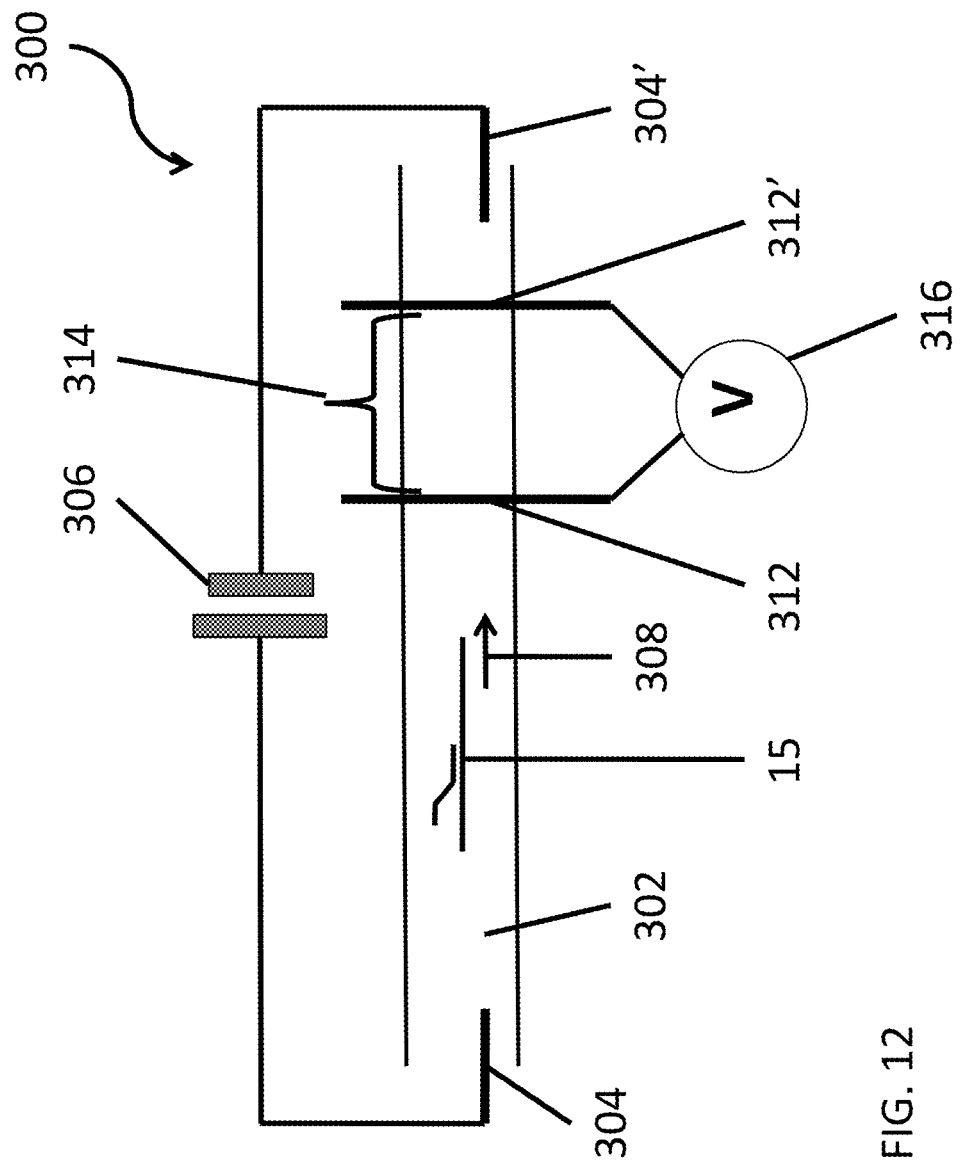
FIG. 12 is a schematic depiction of an assay method in accordance with an embodiment of the invention showing a nanochannel or microchannel apparatus useful for mapping the analytes of embodiments of the present invention.
Figure 13A:
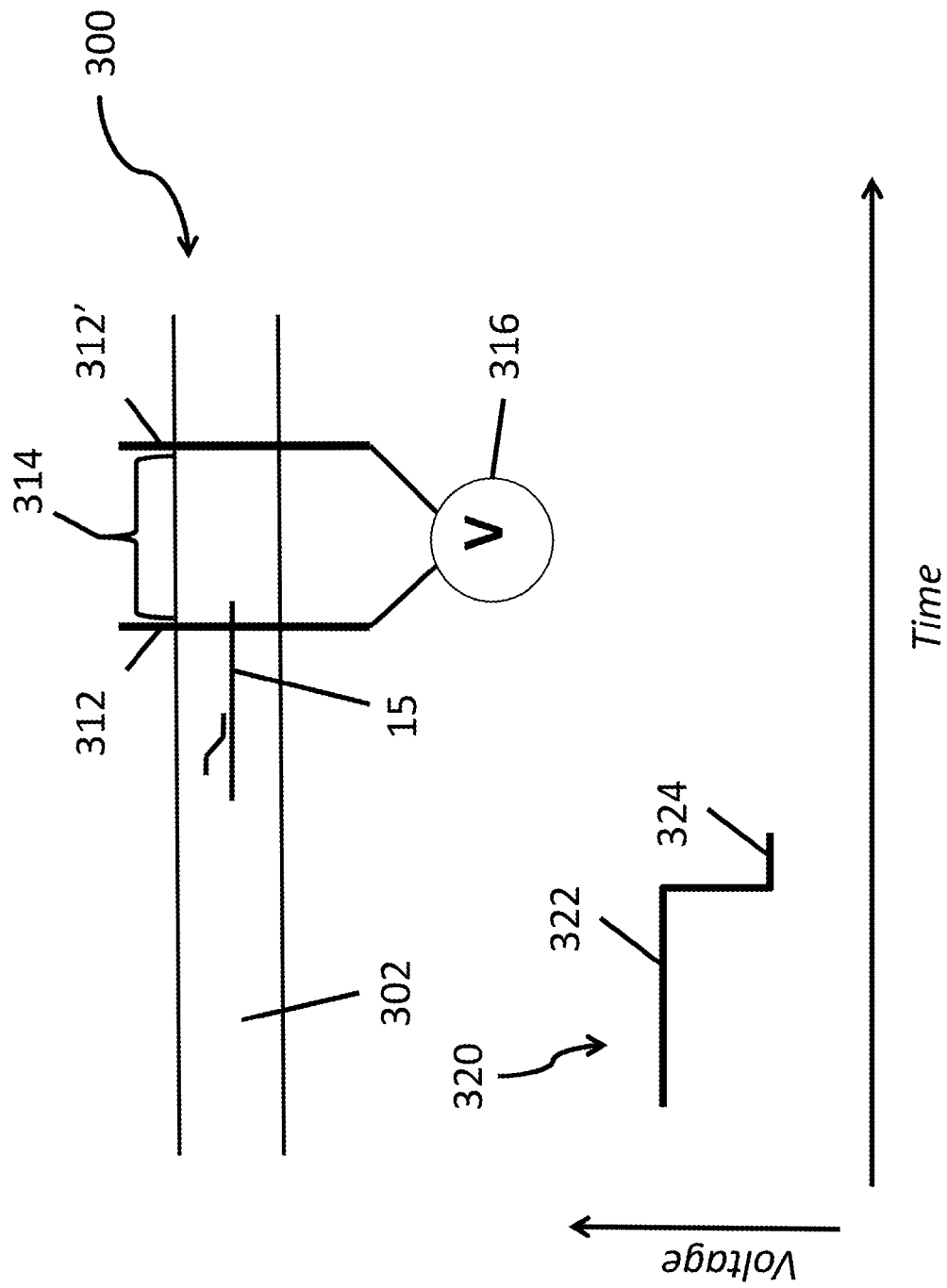
FIG. 13a is a schematic depiction of an assay method in accordance with an embodiment of the invention showing an electrical potential measurement as a DNA molecule having a tagged probe enters a detection volume in the apparatus of FIG. 12.
Figure 13B:
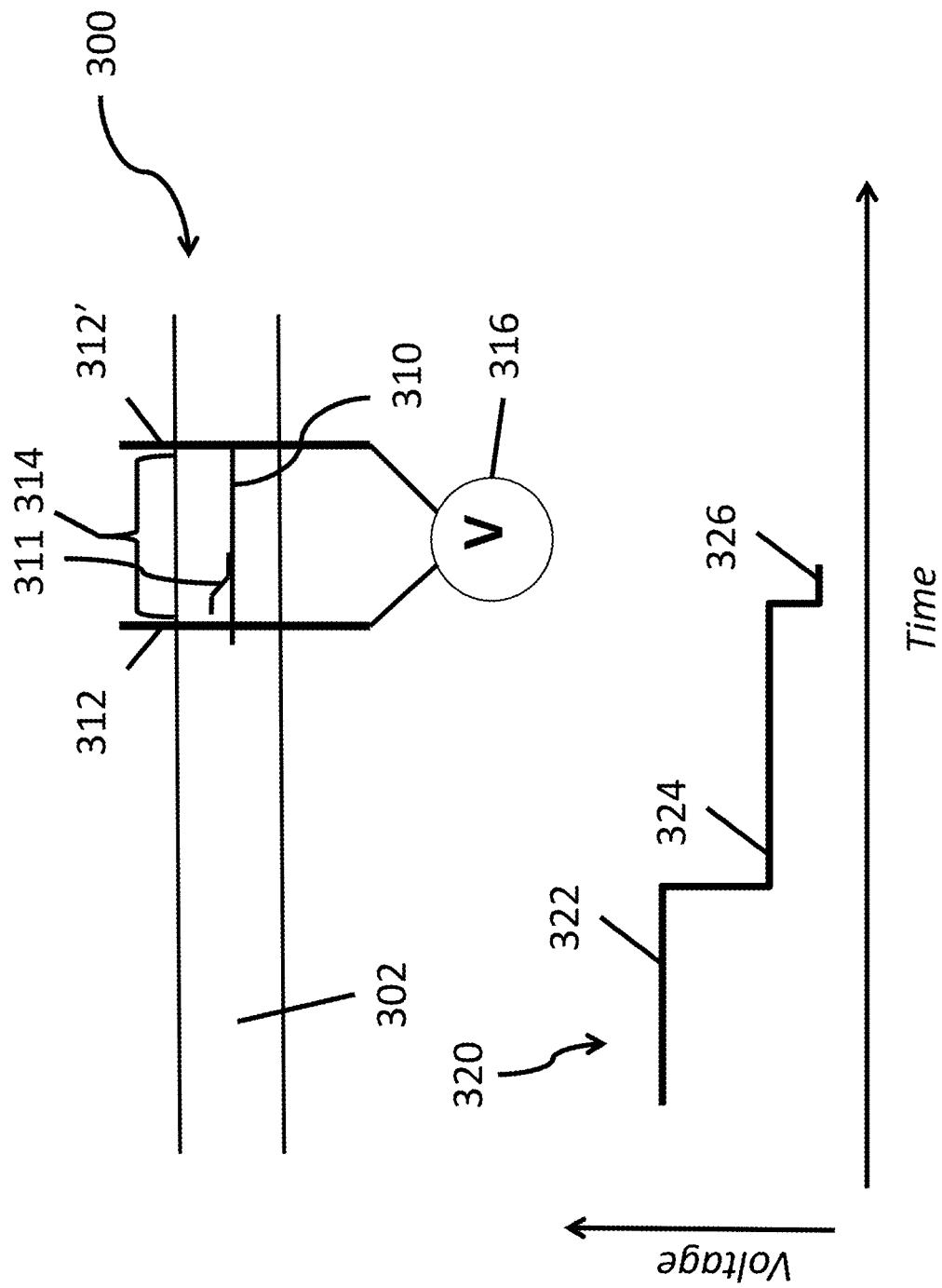
FIG. 13b is a schematic depiction of an assay method in accordance with an embodiment of the invention showing an electrical potential measurement as a tagged probe on a DNA molecule enters a detection volume in the apparatus of FIG. 12.
Figure 13C:
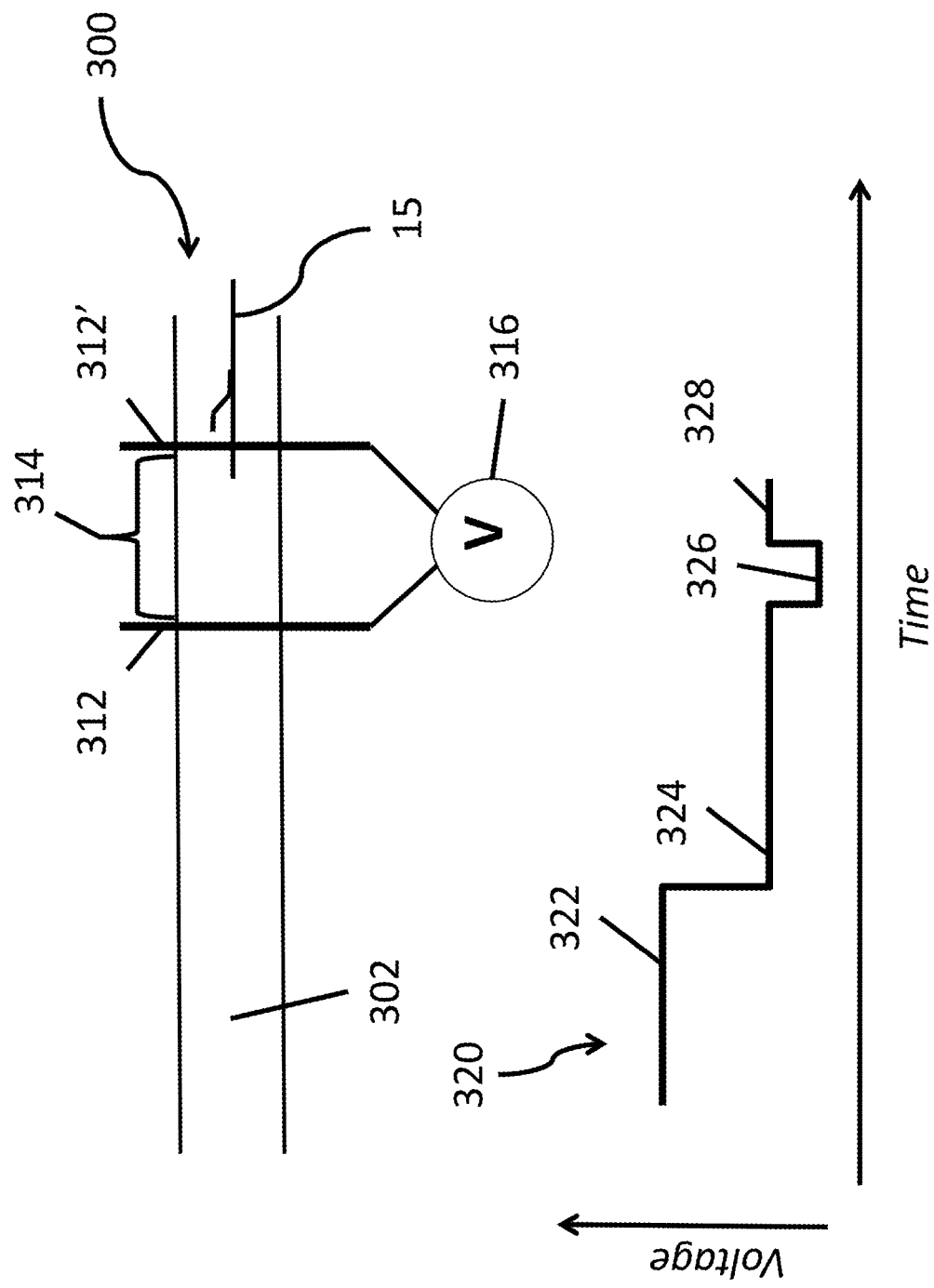
FIG. 13c is a schematic depiction of an assay method in accordance with an embodiment of the invention showing an electrical potential measurement as a tagged probe on a DNA molecule exits a detection volume in the apparatus of FIG. 12.
Figure 13D:
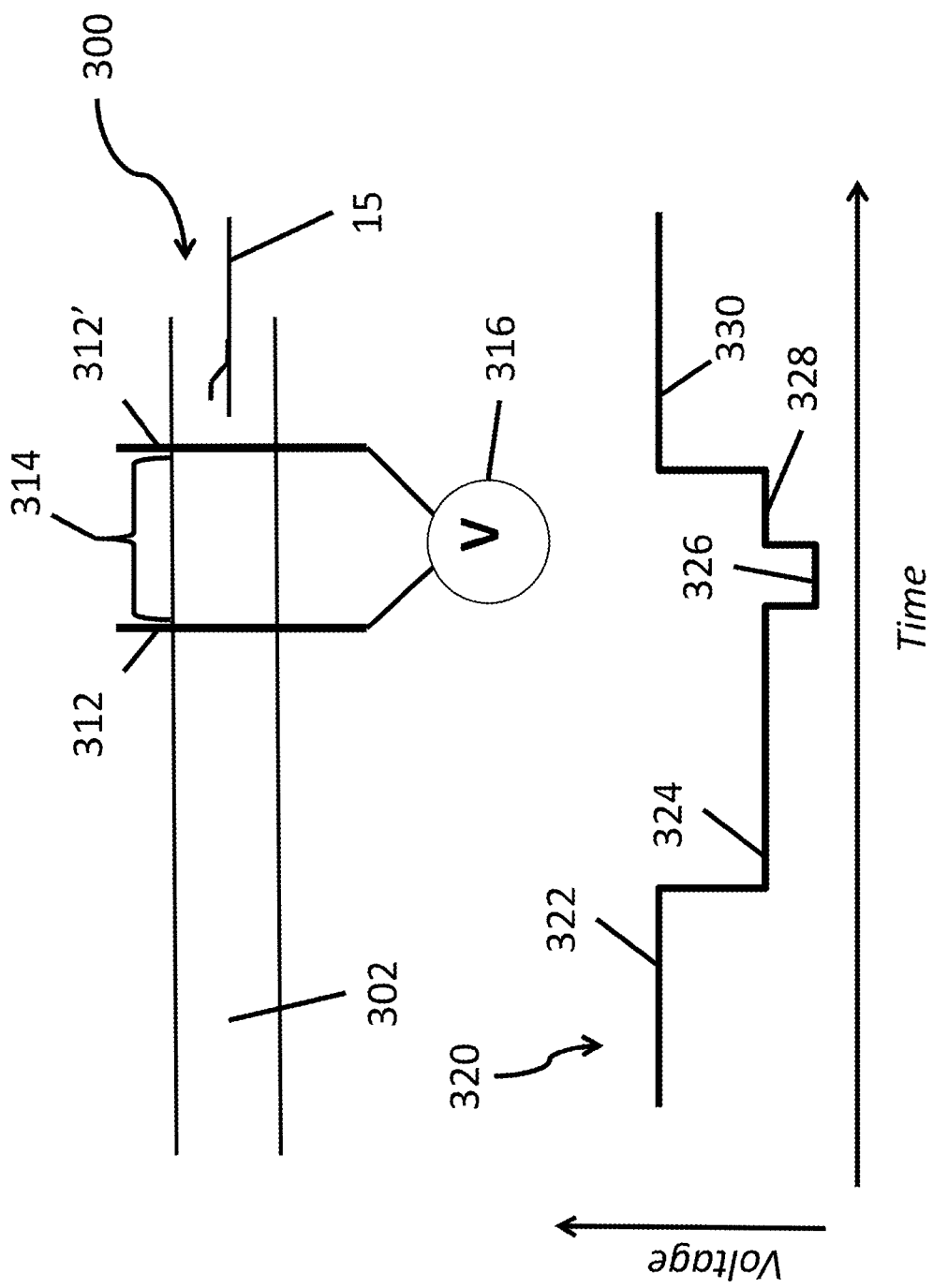
FIG. 13d is a schematic depiction of an assay method in accordance with an embodiment of the invention showing an electrical potential measurement as a DNA molecule having a tagged probe exits a detection volume in the apparatus of FIG. 12.
Figure 14:
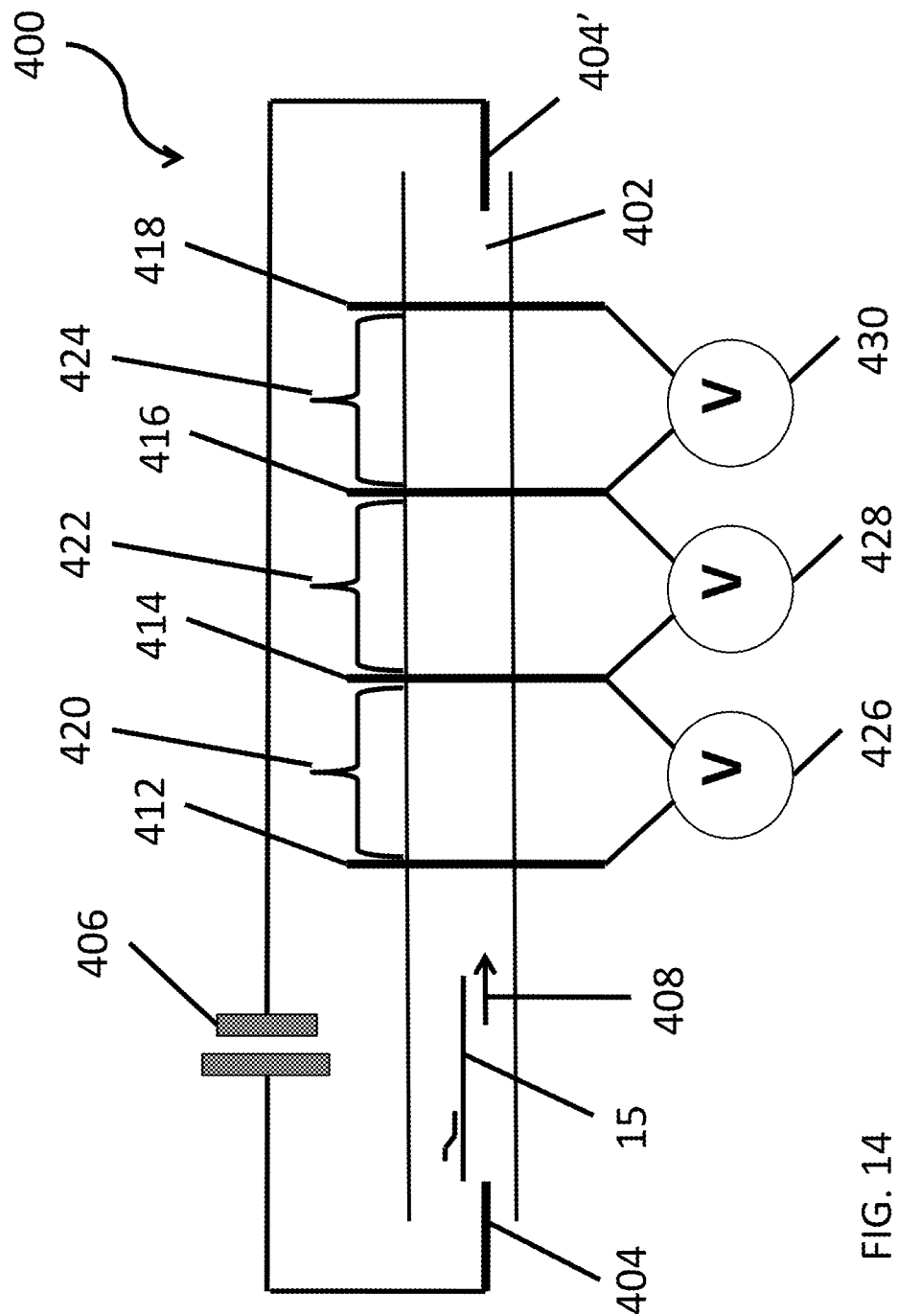
FIG. 14 is a schematic depiction of an assay method in accordance with an embodiment of the invention showing a nanochannel or microchannel apparatus having multiple detection volumes.

In another embodiment, an electrical property such as electrical potential or current is measured during translocation of a DNA strand through a nanochannel or microchannel as shown in FIGS. 12 through 14. One embodiment of a fluidic channel apparatus is shown schematically in FIG. 12. In FIG. 12, the apparatus 300 includes a fluidic microchannel or nanochannel 302. The fluidic channel may be a microchannel having a width selected from a range of about 1 μm to about 25 μm or a nanochannel having a width selected from a range of about 10 nm to about 1000 nm. In the case of a microchannel, the depth may be selected from a range of about 200 nm to about 5 μm, whereas in the case of a nanochannel, the depth may be selected from a range of about 10 nm to about 1000 nm. In either case, the channel may have a length selected from a range of about 1 μm to about 10 cm.

A first pair of electromotive electrodes 304, 304' is connected to a voltage source 306 and positioned in a spaced apart relationship in the channel. When a potential is applied to the electromotive electrodes, these electrodes provide an electrical current along the channel and may be used to provide or enhance a driving force 308 to an analyte 15 in the channel. Other driving forces such as pressure or chemical gradients are contemplated as well. A second pair of electrodes 312, 312', i.e., detector electrodes, is positioned preferably substantially perpendicular to the channel in a spaced apart relationship to define a detection volume 314. The second pair of detector electrodes 312, 312' is connected to a detector 316, such as a voltmeter, which monitors an electrical property in the detection volume 314. In an embodiment where the detector 316 is a voltmeter, an electrical potential between the pair of detector electrodes 312, 312', is measured across the detection volume 314.

The operation of the device is depicted schematically in FIGS. 13*a*-13*d* in which changes in an electrical property across a fluidic channel are monitored, as the analyte 15 is translocated therethrough, with the changes in the electrical property being indicative of probe-containing and probe-free regions. In FIGS. 13*a*-13*d*, the first pair of electromotive electrodes 304, 304' and the current source 306 have been omitted for clarity. In FIG. 13*a*, the fluidic channel 302 contains an analyte 15 traveling therethrough. An electrical property, in this case electrical potential, is measured and recorded across the detection volume 314 by the detector electrodes 312, 312' and the detector 316. The analyte 15 is a DNA template upon which probes have been hybridized using the methods described previously. The DNA template and/or the probe may be coated with a binding moiety, such as the protein RecA, to enhance detection.

Prior to the entry of the analyte 15 into the detection volume 314, a substantially constant voltage 322 is measured across the detection volume. This voltage is shown in the waveform 320 of FIG. 13*a*. As the analyte 15 enters the detection volume 314, it causes an interruption or decrease in the electrical property measured in the detection volume. This interruption or decrease causes a first trough 324 to be exhibited in the waveform 320.

FIG. 13*b* shows the device and waveform 320 once the portion of the target analyte 15 including the probe has entered the detection volume 314. Entry of the probe into the detection volume 314 causes a further interruption or decrease in the electrical property measured in the detection volume. This further interruption or decrease causes a second trough 326 to be exhibited in the waveform 320.

In FIG. 13*c*, the portion of the analyte 15 containing the probe has exited the detection volume 314; however, a distal portion of the analyte 15 may still be present in the detection volume. As a result, the waveform 320 has returned to a level 328 approximating that detected when the initial portion of the analyte first entered the detection volume.

Finally, as shown in FIG. 13*d*, the analyte 15 has fully exited the detection volume 314. As a result, the waveform 320 has returned to a level 330 approximating that detected prior to initial entry of the analyte into the detection volume. Analysis of the waveform 320 permits differentiation between probe-containing and probe-free regions of the analyte, based, at least in part, on the detected changes in the electrical property. As such, it is possible to determine probe locations and map at least a portion of the analyte.

Another embodiment of a fluidic channel apparatus is shown in FIG. 14. In FIG. 14, the apparatus 400 comprises a fluidic microchannel or nanochannel 402. As before, the fluidic channel may be a microchannel having a width selected from a range of about 1 μm to about 25 μm or a nanochannel having a width selected from a range of about 10 nm to about 1 μm. In the case of a microchannel, the depth may be selected from a range of about 200 nm to about 5 μm, whereas in the case of a nanochannel, the depth may be selected from a range of about 10 nm to about 1 μm. In either case, the channel may have a length selected from a range of about 1 μm to about 10 cm.

A first pair of electromotive electrodes 404, 404' is connected to a voltage source 406 and positioned in a spaced apart relationship in the channel. When a potential is applied to the electromotive electrodes, these electrodes provide an electrical current along the channel and may be used to provide or enhance a driving force 408 to an analyte 15 in the channel. Other driving forces such as pressure or chemical gradients are contemplated as well. Multiple detector electrodes 412, 414, 416, 418, are positioned preferably perpendicular to the channel in a spaced apart relationship to define a plurality of detection volumes between adjacent detector electrodes. Thus, as seen in FIG. 14, detector electrodes 412 and 414 define detection volume 420, detector electrodes 414 and 416 define detection volume 422, and detector electrodes 416 and 418 define detection volume 424. The detector electrodes are each connected to detectors 426, 428, 430 such as voltmeters, which monitor an electrical property in each detection volume. In the embodiment where the detectors are voltmeters, a drop in electrical potential is measured across each detection volume. Operation of the apparatus is similar to that of the system of FIGS. 13*a*-13*d*, with the exception that additional waveforms are generated due to the presence of additional detection volumes. The additional waveforms may be combined to further improve the quality of the data being generated by the device.

It should be understood that number of detector electrodes and detection volumes is not intended to limited to those depicted in FIG. 14. Rather, any number of detection volumes may be included along the length of the fluidic channel. Further, the detector electrodes and detection volumes need not be evenly spaced, evenly sized or directly adjacent to one another. Various detection volume sizes, spacing and configurations are contemplated.

EQUIVALENTS

Those skilled in the art will readily appreciate that all parameters listed herein are meant to be exemplary and actual parameters depend upon the specific application for which the methods and materials of embodiments of the present invention are used. It is, therefore, to be understood that the foregoing embodiments are presented by way of example only and that, within the scope of the appended claims and equivalents thereto, the invention may be practiced otherwise than as specifically described.

The described embodiments of the invention are intended to be merely exemplary and numerous variations and modifications will be apparent to those skilled in the art. All such variations and modifications are intended to be within the scope of the present invention as defined in the appended claims.

---

What is claimed is:

1. A method for producing a biomolecule analyte, the method comprising:
   a) providing a single-stranded DNA or RNA template comprising (i) two or more secondary structures and (ii) a plurality of probe recognition sites comprising at least two different types of nucleotide recognition sites complementary to at least two different types of sequence-specific oligonucleotide probes, wherein each type of nucleotide recognition sites of the at least two different types of nucleotide recognition sites comprises multiple identical nucleotide recognition sites;
   b) hybridizing a first type of the at least two different types of sequence-specific oligonucleotide probes to the template such that multiple probes of the first type of the at least two different types of sequence-specific oligonucleotide probes bind to the multiple identical nucleotide recognition sites of the first type of nucleotide recognition sites of the at least two different types of recognition sites and form a hybridized template comprising multiple probes of the first type of the at least two different types of sequence-specific oligonucleotide probes;
   c) after the hybridizing step, conducting a base extension reaction from a 3' end of each of the multiple probes of the first type of the at least two different types of sequence-specific oligonucleotide probes along the hybridized template comprising multiple probes of the first type of the at least two different types of sequence-specific oligonucleotide probes;
   d) terminating the base-extension reaction after step c) is conducted for a time period such that (i) the multiple probes of the first type of the at least two different types of sequence-specific oligonucleotide probes are securely hybridized to the template and (ii) other types of recognition sites of the at least two different types of recognition sites of the hybridized template are left unoccupied, thereby forming a base extension product comprising the hybridized template;
   e) after step d), applying heat or chemicals to the base extension product to denature the hybridized template such that at least a portion of said two or more secondary structures of the hybridized template is broken, thereby forming a denatured DNA or RNA comprising the multiple probes of the first type of the at least two different types of sequence-specific oligonucleotide probes; and
   f) thereafter, performing steps b) to d) by hybridizing a second type of the at least two different types of sequence-specific oligonucleotide probes to the denatured DNA or RNA, thereby producing the biomolecule analyte, wherein the biomolecule analyte comprises DNA or RNA (i) comprising a reduced number of the secondary structures and (ii) comprising multiple probes of the first type of the at least two different types of sequence-specific oligonucleotide probes and multiple probes of the second type of the at least two different types of sequence-specific oligonucleotide probes, wherein the first type of the at least two different types of sequence-specific oligonucleotide probes and the second type of the at least two different types of sequence-specific oligonucleotide probes have different nucleotide sequences and are hybridized to different types of nucleotide recognition sites of the at least two different types of nucleotide recognition sites.

2. The method of claim 1, wherein the denaturing step comprises applying the heat to the base extension product.

3. The method of claim 1, wherein at least a portion of the at least two different types of sequence-specific oligonucleotide probes comprises tagged probes.

4. The method of claim 1, wherein at least a portion of the template or the at least two different types of sequence-specific oligonucleotide probes is coated with a protein.

5. The method of claim 1, wherein step b) is performed at a temperature ≥a first Tm wherein the first Tm is the melting temperature of the first type of the at least two different types of sequence-specific oligonucleotide probes and the hybridizing step in step f) is performed at a temperature ≥a second Tm, wherein the second Tm is the melting temperature of the second type of the at least two different types of sequence-specific oligonucleotide probes.

6. The method of claim 1, wherein step c) is conducted at a temperature ≥a first Tm wherein the first Tm is the melting temperature of the first type of the at least two different types of sequence-specific oligonucleotide probes and the base extension reaction in step f) is conducted at a temperature ≥a second Tm wherein the second Tm is the melting temperature of the second type of the at least two different types of sequence-specific oligonucleotide probes.

7. A method for analyzing a biomolecule analyte comprising the steps of:
   a) producing the biomolecule analyte using the method of claim 1;
   b) disposing the biomolecule analyte in a fluidic channel, wherein the fluidic channel is a nanochannel or microchannel;
   c) applying a potential along the fluidic channel;
   d) translocating the biomolecule analyte from a first end of the fluidic channel to a second end of the fluidic channel; and
   e) detecting electrical properties cross the fluidic channel as the biomolecule analyte moves through the fluidic channel, thereby analyzing the biomolecule analyte.

* * * * *

SEQUENCE LISTING

```
<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(4)
<223> OTHER INFORMATION: a, c, t, g, unknown or other

<400> SEQUENCE: 1
annncgagac t                                                            11

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttctagatt ctag                                                         14

<210> SEQ ID NO 3
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cuucuagauu cuag                                                         14

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (8)..(10)
<223> OTHER INFORMATION: a, c, t, g, unknown or other

<400> SEQUENCE: 4
agtctcgnnn t                                                       11
```